United States Patent
Ten Kate et al.

(10) Patent No.: US 11,878,954 B2
(45) Date of Patent: *Jan. 23, 2024

(54) PROCESS FOR MANUFACTURING ETHYLENEAMINE COMPOUNDS

(71) Applicant: NOURYON CHEMICALS INTERNATIONAL B.V., Arnhem (NL)

(72) Inventors: Antoon Jacob Berend Ten Kate, Arnhem (NL); Rolf Krister Edvinsson, Partille (SE); Michiel Jozef Thomas Raaijmakers, Deventer (NL); Rens Veneman, Amersfoort (NL); Slavisa Jovic, Utrecht (NL); Lawien Zubeir, Deventer (NL); Eike Nicolas Kantzer, Uddevalla (SE); Ina Ehlers, Stenungsund (SE); Hendrik Van Dam, Ede (NL); Karl Fredrik Lake, Södertälje (SE)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 238 days.

This patent is subject to a terminal disclaimer.

(21) Appl. No.: 17/310,608

(22) PCT Filed: Feb. 13, 2020

(86) PCT No.: PCT/EP2020/053737
§ 371 (c)(1),
(2) Date: Aug. 13, 2021

(87) PCT Pub. No.: WO2020/165330
PCT Pub. Date: Aug. 20, 2020

(65) Prior Publication Data
US 2022/0024853 A1 Jan. 27, 2022

(30) Foreign Application Priority Data
Feb. 13, 2019 (EP) .................................. 19156904

(51) Int. Cl.
*C07C 213/08* (2006.01)
*C07C 213/10* (2006.01)
*C07C 209/16* (2006.01)
*C07C 209/60* (2006.01)
*C07C 209/62* (2006.01)
*C07C 209/68* (2006.01)
*C07C 209/86* (2006.01)
*C07C 213/02* (2006.01)

(52) U.S. Cl.
CPC .......... *C07C 213/10* (2013.01); *C07C 209/16* (2013.01); *C07C 209/60* (2013.01); *C07C 209/62* (2013.01); *C07C 209/68* (2013.01); *C07C 209/86* (2013.01); *C07C 213/02* (2013.01); *C07C 213/08* (2013.01)

(58) Field of Classification Search
None
See application file for complete search history.

(56) References Cited

U.S. PATENT DOCUMENTS 11,072,686 B2 7/2021 Veneman et al.
2010/0087681 A1* 4/2010 Petraitis ................ C07C 211/14
564/470

FOREIGN PATENT DOCUMENTS

| CN | 111032618 A | 4/2020 |
| WO | 2010042158 A1 | 4/2010 |
| WO | 2016042168 A1 | 3/2016 |
| WO | 2018166938 A1 | 9/2018 |

OTHER PUBLICATIONS

Haynes et al. (CRC Handbook of Chemistry and Physics, 94 Ed., 2014, Section 15: Practical Laboratory Data, Laboratory Solvents and Other Liquid Reagents) (Year: 2014).*

* cited by examiner

Primary Examiner — Sudhakar Katakam
Assistant Examiner — Jennifer C Sawyer
(74) Attorney, Agent, or Firm — LORENZ & KOPF, LLP

(57) ABSTRACT

Process for manufacturing ethyleneamine compounds selected from the group of ethyleneamines and hydroxyethylethyleneamines wherein the process comprises two reaction sequences.

16 Claims, 7 Drawing Sheets

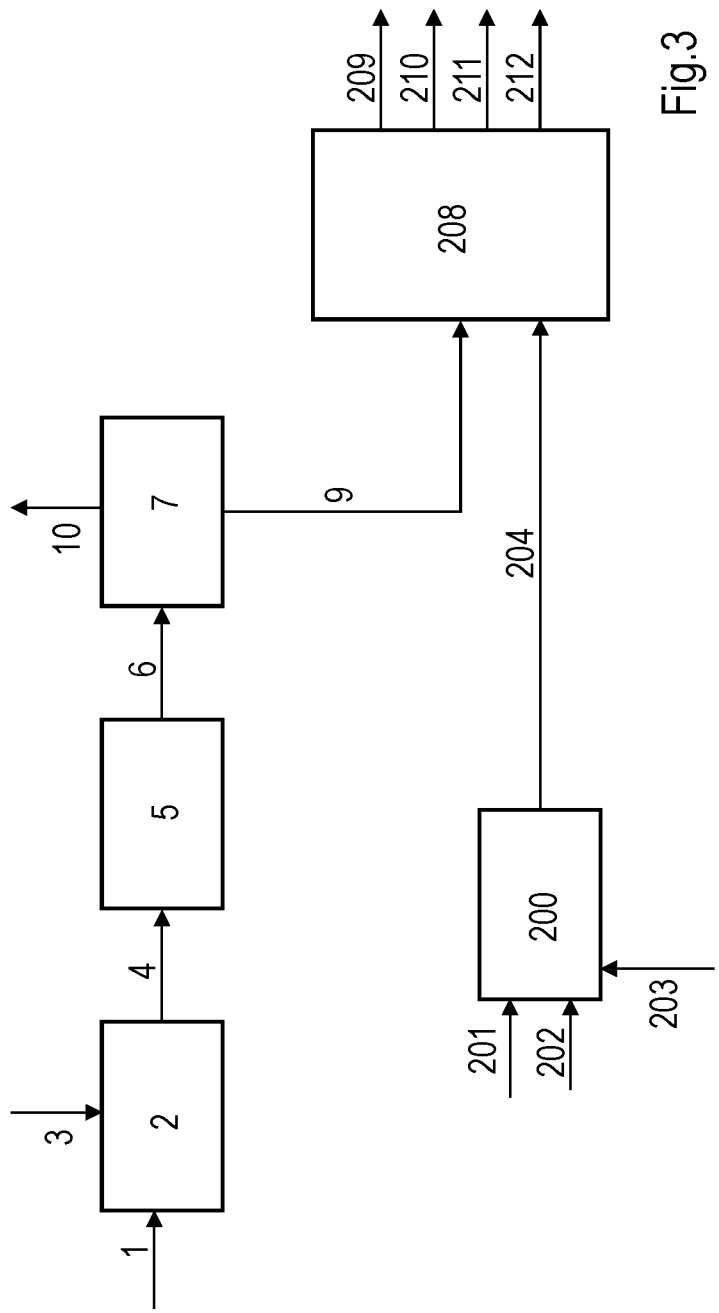

PROCESS FOR MANUFACTURING ETHYLENEAMINE COMPOUNDS

CROSS-REFERENCE TO RELATED APPLICATION

This application is a U.S. National-Stage entry under 35 U.S.C. § 371 based on International Application No. PCT/EP2020/053737, filed Feb. 13, 2020, which was published under PCT Article 21(2) and which claims priority to European Application No. 19156904.5, filed Feb. 13, 2019, which are all hereby incorporated in their entirety by reference.

TECHNICAL FIELD

The disclosure pertains to the manufacture of ethyleneamine compounds selected from the group of ethyleneamines, and hydroxyethylethyleneamines.

BACKGROUND

Ethyleneamine compounds, more specifically ethyleneamines and hydroxyethylethyleneamines, are useful in many applications.

Ethyleneamines consist of two or more nitrogen atoms linked by ethylene units. Ethyleneamines can be present in the form of linear chains H2N(—CH2-CH2-NH)p-H. For p=1, 2, 3, 4, . . . this gives, respectively, ethylenediamine (EDA), diethylenetriamine (DETA), linear triethylenetetramine (L-TETA), and linear tetraethylenepentamine (L-TEPA). As will be clear, this range can be extended. With three or more ethylene units it is also possible to create branched ethyleneamines such as N(CH2-CH2-NH2)3, trisaminoethylamine (TAEA). Two adjacent nitrogen atoms can be connected by two ethylene units to form a piperazine ring. Piperazine rings can be present in longer chains to produce the corresponding piperazine-ring-containing ethyleneamines.

Ethyleneamines, in particular diethylenetriamine (DETA) and further higher ethyleneamines such as linear triethylenetetramine (L-TETA) and linear tetraethylenepentamine (L-TEPA), are attractive products from a commercial point of view. In particular, the interest in higher ethyleneamines is increasing as these compounds have numerous commercial applications, e.g., as starting materials for, or use in, asphalt additives, corrosion inhibitors, epoxy curing agents, fabric softeners, fuel additives, hydrocarbon purification, ion exchange resins, lube oil additives, paper wet-strength resins, petroleum production chemicals, solvents, synthetic resins such as amide resins, mineral processing aids and interface-active substances (surfactants).

Hydroxyethylethyleneamines find application in chemical processes, as solvent or as reactant. For example, aminoethylethanolamine or AEEA of the formula H2N-CH2-CH2-NH—CH2-CH2-OH is an organic base used in the industrial manufacture of fuel and oil additives, chelating agents, and surfactants. Chain-extended ethanolamines, e.g., monoethanolamine compounds of the formula H2N—(CH2-CH2-NH)q-CH2-CH2-OH, wherein q is 2 or higher, are interesting intermediates for various types of organic synthesis, e.g., the manufacturing of esters of carboxylic acids. They can also be used in, for example, the formation of synthetic resins, as surfactants, for the production of emulsifiers, in fabric softeners, and as epoxy curing agents.

Today, the EDC-based process is the main process for producing higher ethyleneamines, defined for the purposes of the present specification as ethyleneamines with at least two ethylene moieties. The EDC route is the substitution reaction of EDC (ethylenedichloride) with ammonia and/or an ethyleneamine at elevated temperatures and pressures to form hydrochloride salts of ethyleneamines which are then reacted with caustic to generate mixtures of ethyleneamines and NaCl. The EDC route has its disadvantages. It is dependent on the use of ethylenedichloride which is expensive, difficult to handle, and connected to HSE issues. Additionally, the EDC route gives a mixture of many different ethyleneamines Nevertheless, as demonstrated by its widespread use, it remains an attractive process for manufacturing ethyleneamines.

In view of the fluctuating market conditions for ethyleneamine compounds and for the starting materials used in their manufacture there is need in the art for a process which allows flexibility in the products produced, and in the starting materials used. There is also need in the art for a process which combines flexibility for the starting materials and products used with efficient use of apparatus and efficient processing of waste streams. The present disclosure provides a process which addresses these issues. In addition, other objects, desirable features and characteristics will become apparent from the subsequent summary and detailed description, and the appended claims, taken in conjunction with the accompanying drawings and this background.

BRIEF SUMMARY

This disclosure provides a process for manufacturing ethyleneamine compounds selected from the group of ethyleneamines and hydroxyethylethyleneamines, wherein the process comprises two reaction sequences, the first reaction sequence comprising the steps of:
in an adduction step, providing a CO2 adduct of a starting compound comprising a —NH—CH2-CH2-NH— moiety or a —NH—CH2-CH2-OH moiety, or HO—CH2-CH2-OH,
in a chain-extension step, reacting a hydroxy-functional compound selected from ethanolamines and dihydroxyethane with an ethyleneamine compound, wherein at least part of a total of hydroxy-functional compounds and the ethyleneamine compound is provided in the form of a CO2 adduct, to form a CO2 adduct of a chain-extended ethyleneamine compound,
in an elimination step, converting the CO2 adduct of the chain-extended ethyleneamine compound to the corresponding product ethyleneamine compound by removal of the carbonyl group, and the second reaction sequence comprising the steps of:
in an amination step, reacting monoethanolamine with ammonia in the presence of hydrogen and an amination catalyst to form a reaction mixture comprising ethylenediamine,
in a separation step, separating the reaction mixture derived from the amination step into at least two fractions,
wherein the first reaction sequence and the second reaction sequence are connected in that at least one of the following takes place:
an effluent from a step in the first reaction sequence is provided as a starting material to a step in the second reaction sequence,
an effluent from a step in the second reaction sequence is provided as a starting material to a step in the first reaction sequence, a step of the first reaction sequence and a step of the second reaction sequence are combined, or an effluent from a step in the first reaction sequence is combined with an effluent from a step in the second reaction sequence.

BRIEF DESCRIPTION OF THE DRAWINGS

The present disclosure will hereinafter be described in conjunction with the following drawing Figs., wherein like numerals denote like elements, and:

FIG. 3 illustrates a further embodiment of the process as contemplated herein.

DETAILED DESCRIPTION

Figure 1:
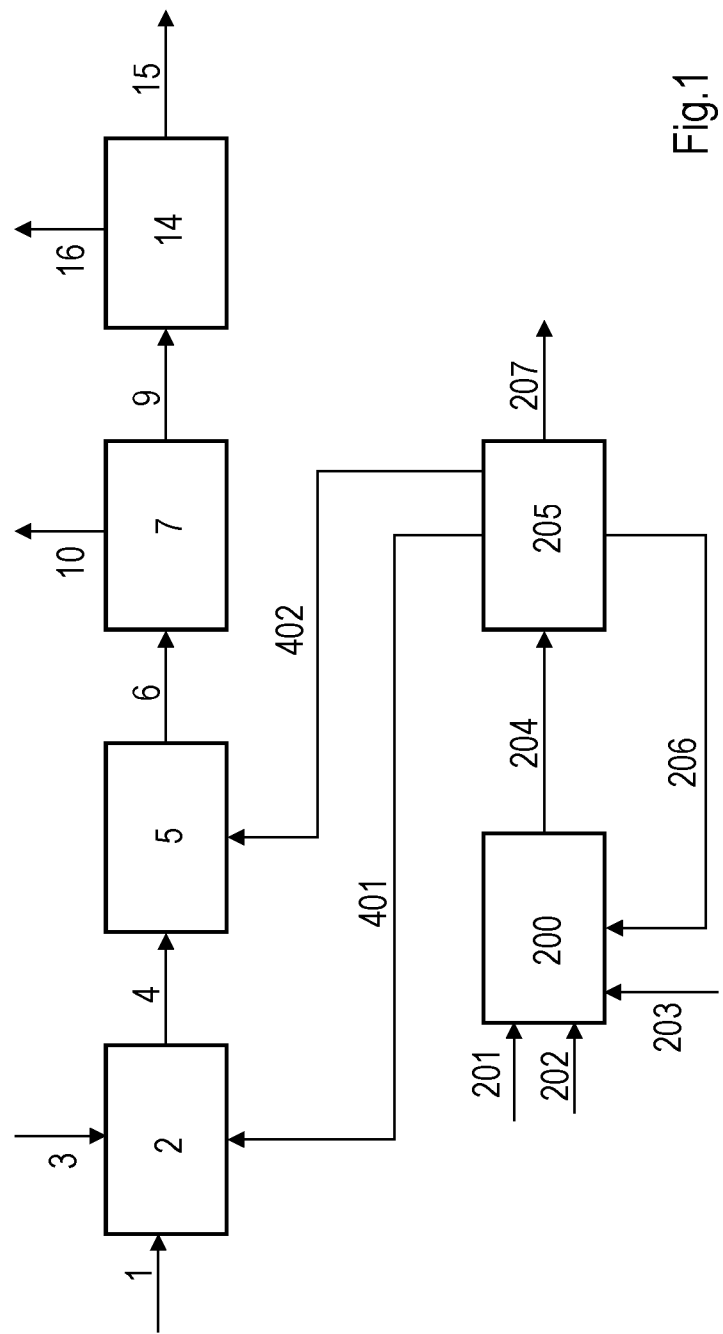
FIG. 1 illustrates a first embodiment of the process as contemplated herein.

The following detailed description is merely exemplary in nature and is not intended to limit the disclosure or the application and uses of the disclosure. Furthermore, there is no intention to be bound by any theory presented in the preceding background of the disclosure or the following detailed description.

The disclosure pertains to a process for manufacturing ethyleneamine compounds selected from the group of ethyleneamines and hydroxyethylethyleneamines wherein the process comprises two reaction sequences, the first reaction sequence comprising the steps of in an adduction step providing a CO2 adduct of a starting compound comprising a —NH—CH2-CH2-NH— moiety or a —NH—CH2-CH2-OH moiety, or HO—CH2-CH2-OH, in a chain-extension step reacting a hydroxy-functional compound selected from ethanolamines and dihydroxyethane with an ethyleneamine compound, wherein at least part of the total of hydroxy-functional compounds and ethyleneamine compound is provided in the form of a CO2 adduct, to form a CO2 adduct of a chain-extended ethyleneamine compound, in an elimination step converting a CO2 adduct of a chain-extended ethyleneamine compound to the corresponding product ethyleneamine compound by removal of the carbonyl group, and the second reaction sequence comprising the steps of in an amination step reacting monoethanolamine with ammonia in the presence of hydrogen and an amination catalyst to form a reaction mixture comprising ethylenediamine, in a separation step separating the reaction mixture derived from the amination step into at least two fractions, with the first reaction sequence and the second reaction sequence being connected in that at least one of the following takes place:

effluent from a step in the first reaction sequence is provided as starting material to a step in the second reaction sequence, effluent from a step in the second reaction sequence is provided as starting material to a step in the first reaction sequence, a step of the first reaction sequence and a step of the second reaction sequence are combined, or effluent from a step in the first reaction sequence is combined with effluent from a step in the second reaction sequence.

The process as contemplated herein uses two connected reaction sequences for the manufacture of ethyleneamine compounds. Each reaction sequence has its own advantages. The process of the first reaction sequence allows the manufacture of high molecular weight ethyleneamine compounds, in particular straight-chain compounds. The process of the second reaction sequence allows the manufacture in an efficient manner of a reaction product comprising a mixture of many different ethyleneamine compounds, some of which are interesting as products in themselves while others may be more attractive as starting materials for the manufacture of higher ethyleneamine compounds. As will be discussed in more detail below, the process as contemplated herein allows for flexibility in starting materials used and products produced, and an efficient use of apparatus.

A particular advantage of the process as contemplated herein is that it makes it possible to produce a wide range of ethyleneamine products from ammonia and monoethanolamine. In one embodiment, ethylenediamine formed in the second reaction sequence from monoethanolamine and ammonia is provided to the first reaction sequence, where it is reacted with monoethanolamine. In this manner, a variety of products can be obtained from widely available starting materials. In a further embodiment, the monoethanolamine provided to either or both reaction sequences is obtained from reacting ethyleneoxide with ammonia, allowing the use of even more widely available starting materials.

A further advantage is that ethanolamine compounds such as aminoethylethanolamine which may be formed as a side product in the second reaction sequence may be processed via the first reaction sequence, resulting in an efficient use of available equipment.

A further advantage is that specific ethyleneamine compounds containing piperazine rings, e.g., piperazinoethyl ethylenediamine (PEEDA), diaminoethylpiperazine, and the piperazine-ring-containing penta- and hexaethyleneamines, can be obtained by providing cyclics such as piperazine and aminoethylpiperazine manufactured in the second reaction sequence to the first reaction sequence.

Further advantages of the present disclosure and specific embodiments thereof will become apparent from the further specification.

In the following, the two individual reaction sequences will be discussed. Then, the various ways in which the reaction sequences can be connected will be discussed.

The First Reaction Sequence

The first reaction sequence comprises the steps of in an adduction step providing a CO2 adduct of a starting compound comprising a —NH—CH2-CH2-NH— moiety or a —NH—CH2-CH2-OH moiety, or HO—CH2-CH2-OH, in a chain-extension step reacting a hydroxy-functional compound selected from ethanolamines and dihydroxyethane with an ethyleneamine compound, wherein at least part of the total of hydroxy-functional compounds and ethyleneamine compound is provided in the form of a CO2 adduct, to form a CO2 adduct of a chain-extended ethyleneamine compound, in an elimination step converting a CO2 adduct of a chain-extended ethyleneamine compound to the corresponding product ethyleneamine compound by removal of the carbonyl group.

Starting materials for the first reaction sequence are a hydroxy-functional compound selected from ethanolamines and dihydroxyethane, and an ethyleneamine compound. The core of the first reaction sequence is that a hydroxy-functional compound reacts with an amine-functional compound with conversion of a primary amine into a secondary amine or a secondary amine into a tertiary amine. For example, a compound exemplified by formula R—OH may react with a compound exemplified by the formula H2NR', to form a compound exemplified by the formula R—NH—R', with formation of water. For a further example, a compound exemplified by formula R—OH may react with a compound exemplified by the formula RNR'R", with formation of water.

Hydroxyl-functional compounds are selected from the group of ethanolamines and dihydroxyethane. In the context of the present specification, the group of ethanolamines encompasses 2-hydroxy-ethylamine, also indicated as monoethanolamine or MEA, and hydroxyethylethyleneamines. Preferred hydroxy-functional compounds include monoethanolamine (MEA), aminoethylethanolamine (AEEA), hydroxyethyldiethylenetriamine (HE-DETA), hydroxyethyltriethylenetetraamine (HE-TETA), and diethanolamine.

The hydroxyl-functional compound is reacted with an ethyleneamine compound. Ethyleneamine compounds comprise at least one —NH2 group. Preferred ethyleneamine compounds include ethylenediamine (EDA), N-methylethylenediamine (MeEDA), diethylenetriamine (DETA), piperazine (PIP), N-aminoethylpiperazine (AEP), triethylene tetramine (TETA), N, N'-diaminoethylpiperazine (DAEP), tetraethylenepentamine (TEPA), and pentaethylenehexamine (PEHA).

Ethyleneamine compounds may also encompass ethanolamines as described above. If an ethanolamine is used as ethyleneamine compound, the first reaction sequence will result in the formation of (chain-extended) hydroxyethylethyleneamines. If it is desired to manufacture ethyleneamines, the ethyleneamine compound to be reacted with the hydroxyl-functional compound should not be an ethanolamine, but selected from ethyleneamines that do not contain a hydroxy group.

Some structures of ethyleneamines and hydroxy-functional compounds are provided below:

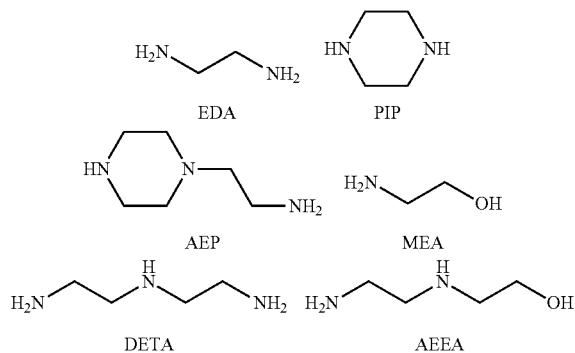

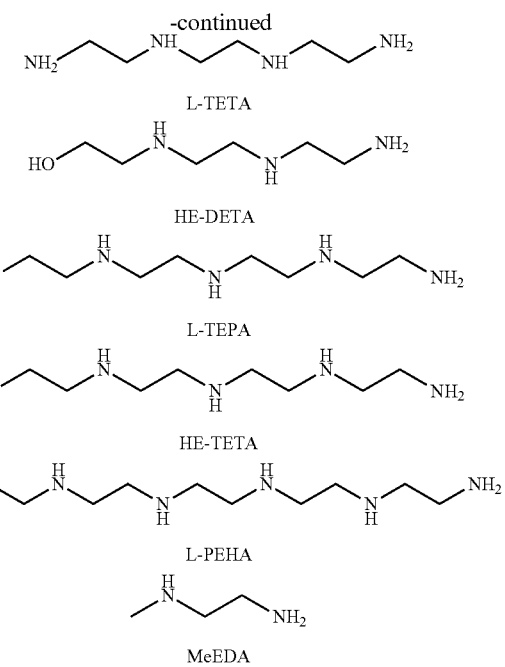

Preferred examples of product polyethyleneamine compounds are triethylene tetramine (TETA), N,N'-diaminoethylpiperazine (DAEP), tetraethylenepentamine (TEPA), pentaethylenehexamine (PEHA), N-[(2-aminoethyl) 2-aminoethyl]piperazine) (PEEDA), and 1-[2-[[2-[(2-aminoethyl)amino]ethyl]amino]ethyl]piperazine) (PEDETA).

Adduction Step

The first step in the first reaction sequence of the present disclosure is an adduction step, in which a CO2 adduct is provided of a starting compound comprising a —NH—CH2-CH2-NH— moiety or a —NH—CH2-CH2-OH moiety, or HO—CH2-CH2-OH. The adduction step can be carried out in various manners.

In one embodiment, the adduction step comprises the step of reacting gaseous CO2 with a starting compound comprising a —NH—CH2-CH2-NH— moiety or a —NH—CH2-CH2-OH moiety, or HO—CH2-CH2-OH, resulting in the formation of the respective CO2 adducts. This step is also indicated herein as the absorption step.

In another embodiment of the adduction step, the CO2 adduct is formed by reaction of a starting compound comprising —NH—CH2-CH2-NH— moiety or a —NH—CH2-CH2-OH moiety, or HO—CH2-CH2-OH with a compound not being CO2 which can transfer a carbonyl group to the starting compounds, resulting in the formation of CO2 adducts thereof. These compounds can be indicated as carbon oxide delivering agents.

Carbon oxide delivering agents other than CO2 within the scope of the present disclosure include organic compounds in which a carbonyl moiety is available for being transferred as described above. Organic compounds in which a carbonyl moiety is available include urea and derivatives thereof; linear and cyclic ethylene ureas, especially cyclic ethylene urea, mono or di-substituted ethylene ureas, alkyl and dialkyl ureas, linear and cyclic carbamates, organic carbonates and derivatives or precursors thereof. Such derivatives or precursors may for example include ionic compounds such as carbonate or bicarbonate salts, carbamic acids and associated salts, that can be converted, in some embodiments in situ in the process of the disclosure, into their non-ionic counterparts, for example into linear and cyclic carbamate or urea compounds. When such ionic compounds are used in the present disclosure, they are organic hydrocarbon-based carbonate, bicarbonate or carbamate salts. Preferably the CO delivering agent is CO2 or an organic compound that is suitable for use as a carbon oxide delivering agent, or urea or ethylene carbonate, more preferably the carbon oxide delivering agent is at least partly added as carbon dioxide or urea. The carbon oxide delivering agent can be present in the process in the same molecule as the amine functional or the ethanolamine functional compound by using the aforementioned urea or carbamate compounds.

Examples of carbon oxide delivering agents include

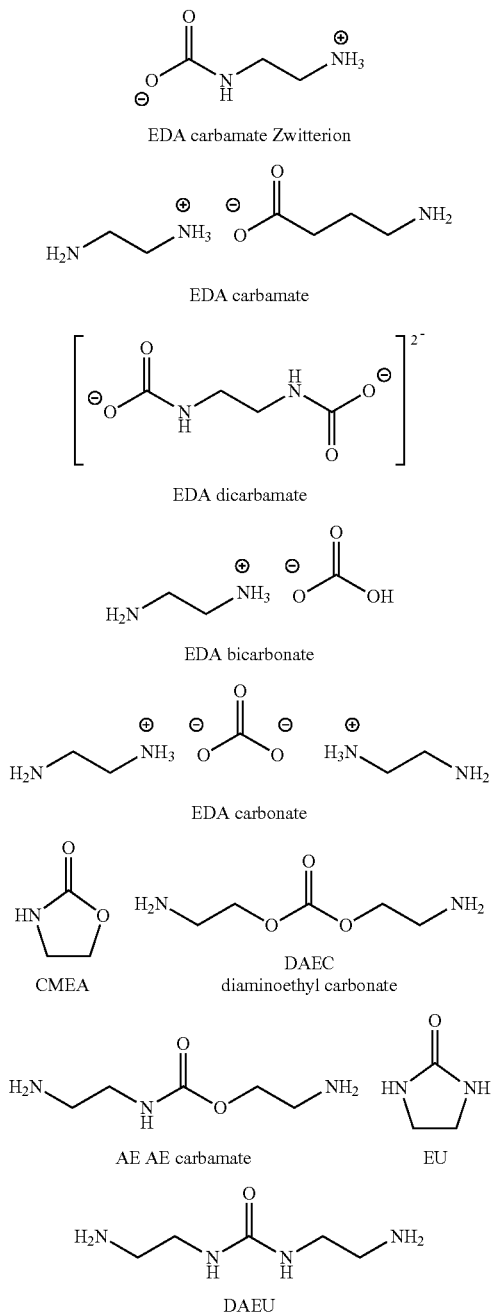

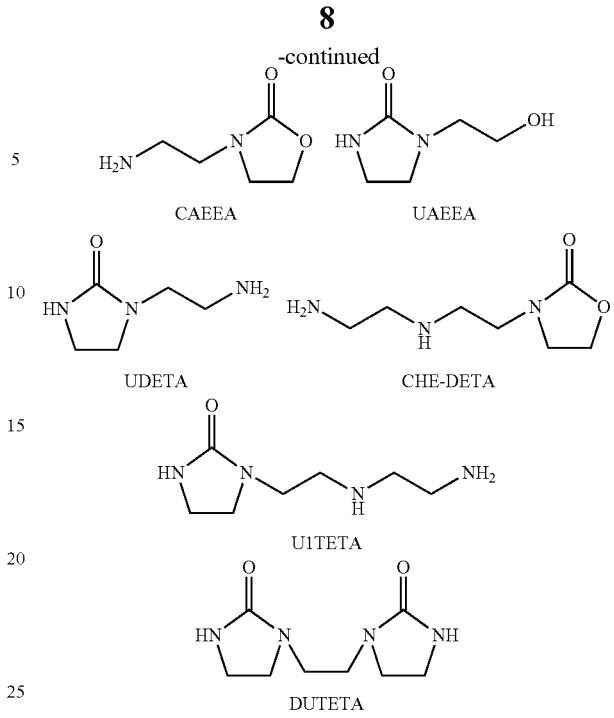

In the above drawing CAEEA again stands for the cyclic carbamate of aminoethylethanolamine, UDETA for the urea of diethylene triamine, DAEU stands for diaminoethyl urea, AE AE carbamate stands for amino ethyl aminoethanol carbamate, CHE-DETA stands for the carbamate of hydroxyethyldiethylene triamine, U1TETA stands for the terminal urea of triethylene tetramine, and DUTETA stands for the 1,3-diurea of triethylene tetramine.

The carbon oxide delivering agent is most preferably added to the reaction in the form of carbon dioxide, urea, the carbamate derivative of the ethanolamine-functional compound or the urea derivative of the ethyleneamine compound, or a combination of these. Examples include CMEA, EU, UDETA, and UAEEA, which is the CO2 adduct of aminoethylethanolamine.

The embodiment of the adduction step in which the CO2 adduct is formed by reaction of a starting compound comprising —NH—CH2-CH2-NH— moiety or a —NH—CH2-CH2-OH moiety, or HO—CH2-CH2-OH with a compound not being CO2 which can transfer a carbonyl group to the starting compounds, can also be indicated as a CO2 transfer step.

In a preferred embodiment of the present disclosure, the adduction step is an absorption step in which CO2 is absorbed in a reaction medium comprising a starting compound comprising a —NH—CH2-CH2-NH— moiety or a —NH—CH2-CH2-OH moiety, or HO—CH2-CH2-OH to form a CO2 adduct of said starting compound and the elimination step is a desorption step in which the CO2 adduct of the product polyethyleneamine compound is reacted with water to form the corresponding ethyleneamine compound and CO2.

Absorption Step

In the absorption step carried out in one embodiment of the process as contemplated herein, CO2 is absorbed in a reaction medium comprising a starting compound comprising a —NH—CH2-CH2-NH— moiety or a —NH—CH2-CH2-OH moiety, or HO—CH2-CH2-OH to form a CO2 adduct of said starting compound. CO2 adducts of these compounds thus include compounds which a —NH—CH2-CH2-NH— moiety is converted to a urea moiety in which two nitrogen atoms are connected via a carbonyl moiety and an ethylene moiety, in accordance with the following formula:

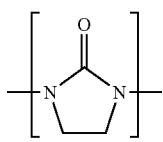

CO2 adducts also include cyclic carbamate compounds

CO2 adducts also include compounds in which the HO—CH2-CH2-OH is converted to a ethylenecarbonate molecule which the two O-atoms of HO—CH2-CH2-OH are connected through via a carbonyl moiety and an ethylene moiety.

In the above, the CO2 adducts are presented as adducts formed by reaction within a single molecule. Of course, CO2 adducts can also be formed by reaction of reactive groups of different molecules. Within the context of the present specification a CO2 adduct moiety is in many embodiments a moiety wherein two nitrogen atoms, or a nitrogen atom and an oxygen atom, or two oxygen atoms, are connected through a —C(O)— moiety. Furthermore CO2 adducts can also form with a single amine or alcohol in a terminal single sided group, i.e. they can be adducts linked to only one nitrogen or oxygen atom.

The absorption step is carried out by contacting CO2 with a reaction medium comprising a starting compound comprising a —NH—CH2-CH2-NH— moiety or a —NH—CH2-CH2-OH moiety, or HO—CH2-CH2-OH to form a CO2 adduct. The contacting step is to be carried out under such conditions that CO2 is absorbed and that a CO2 adduct is formed.

Reaction conditions include a reaction temperature which generally is at least about 120° C. At a temperature below about 120° C., the reaction rate generally is too low to allow meaningful conversion within a reasonable time frame. It may be preferred for the reaction temperature to be at least about 140° C., in particular at least about 150° C., more in particular at least about 170° C. The reaction is generally carried out at a temperature of at most about 400° C. The temperature may thus be at most about 300° C., in particular at most about 250° C., or even at most about 220° C. Operating at a temperature of about 170-about 220° C. is considered preferred.

The pressure during the reaction is determined for the major part by the provision of CO2 to the reaction medium, with the total pressure in the system decreasing during the reaction due to the consumption of CO2. In general, the total pressure in the system is at most about 75 bara. The total pressure generally is at least about 2 bara, in particular at least about 5 bara, more in particular at least about 10 bara.

The amount of CO2 provided to the reaction is not critical. The minimum amount is governed by the amount required to convert the starting material amine compound into its corresponding CO2 adduct. Therefore, the molar ratio between CO2 and —NH—CH2-CH2-NH— moieties, —NH—CH2-CH2-OH moieties, or HO—CH2-CH2-OH generally is at least about 0.1:1. A ratio of at least about 0.2:1, in particular at least about 0.5:1 may be more attractive if more urea adduct is aimed for. A large excess of CO2 is not detrimental to the process, but is generally less attractive for economic reasons. Therefore, as a general maximum a value of about 500:1 may be mentioned. The amount of CO2 dosed will depend on the desired amount of urea adduct in the final product.

In one embodiment, the absorption step is carried out by reacting a compound selected from the group of starting ethyleneamine and hydroxy-functional compounds comprising at least one —NH—CH2-CH2-NH— moiety and at least two ethylene moieties in total, with CO2 in the presence of an auxiliary compound selected from ethylenediamine (EDA), monoethanolamine (MEA) and mixtures thereof, the molar ratio of auxiliary compound to amine compound being at least about 0.02:1.

For the process of this embodiment it is preferred for the ethyleneamine compound to be selected from diethylenetriamine (DETA), triethylenetetramine (L-TETA), aminoethylethanolamine (AEEA), and hydroxyethyldiethylenetriamine (HE-DETA). It is preferred for the molar ratio of auxiliary compound to amine compound to be at least about 0.05:1, in particular at least about 0.1:1, and/or at most about 10:1. It is preferred for the reaction to be carried out at a temperature of at least about 120° C., preferably at least about 140° C., in particular at least about 150° C., more in particular at least about 170° C., and/or at most about 400° C., in particular at most about 350° C., more in particular at most about 300° C., still more in particular at most about 250° C. or even at most about 220° C., for example at a temperature of about 170-about 250° C. or about 170-about 220° C. It is preferred for the molar ratio between CO2 and —NH—CH2-CH2-NH— moieties in the amine compound to be at least about 0.5:1 and/or at most about 500:1. It is preferred for the reaction time to be at most about 10 hours, in particular at most about 6 hours, more in particular at most about 3 hours and/or at least about 5 minutes, in particular between about 0.5 and about 2 hours.

In one embodiment, the absorption step is carried out via a two-step process wherein
  in an absorption step a liquid medium comprising an ethyleneamine compound having a linear NH—CH2-CH2-NH— group is contacted with a CO2-containing gas stream at a pressure of at most about 20 bara, resulting in the formation of a liquid medium into which CO2 has been absorbed,
  bringing the liquid medium to CO2 adduct formation conditions, and in a CO2 adduct formation step forming a CO2 adduct of the ethyleneamine compound, the CO2 adduct formation conditions including a temperature of at least about 120° C., wherein the total pressure at the end of the CO2 adduct formation step is at most about 20 bara, wherein the temperature in the absorption step is lower than the temperature in the CO2 adduct formation step.

By separating the CO2 absorption step from the urea formation step in this embodiment the CO2 absorption step can be carried out at relatively low temperatures and pressures. In the absorption step CO2 is absorbed in the liquid reaction medium. In the reaction step the absorbed CO2 is reacted with the ethyleneamine compound to form an cyclic urea adduct. This means that in the urea formation step the provision of further CO2 is not required, and that the absorption step is carried out until sufficient CO2 has been absorbed in the liquid medium to achieve the desired conversion of ethyleneamine compound into cyclic ureas in the urea formation step. As indicated above, the provision of further CO2 to the reaction medium during the urea formation step (in addition to the CO2 provided during the absorption step) is not required, and generally not attractive because it will increase the pressure during the urea formation step. If so desired for some reason, at most about 20% of the total CO2 required to achieve the desired urea conversion is added during the urea formation step, in particular at most about 10%. In one embodiment of this embodiment, the CO2-containing gas stream comprises at least about 95 vol. % of CO2. In another embodiment of this embodiment, the CO2-containing gas stream comprises at most about 70 vol. % of CO2, in particular at most about 60 vol. % of CO2 and above about 0.01 vol. %, in particular between about 4 and about 60 vol. %. It may be preferred for the step of contacting the liquid medium with the CO2-containing gas steam in the absorption step to be carried out at a temperature between about 0° C. and about 200° C., in particular at a temperature of at most 190° C., more in particular at most about 150° C., or at most about 130° C., more in particular at most about 110° C. and preferably at a value of at least at least about 20° C., in particular at least about 40° C. It may be preferred for the maximum total pressure in the absorption step to be between about 1 and about 15 bara, more in particular between about 1 and about 10 bara, even more in particular between about 1 and about 3 bara. It may be preferred for the temperature in the urea formation step to be at least about 140° C., in particular at least about 150° C., more in particular at least 170° C. and preferably at most about 400° C., in particular at most about 300° C., more in particular at most about 250° C., or even at most about 220° C. The urea formation step is preferably carried out in a closed vessel. It may be preferred for the urea formation step to be carried out in a vessel wherein the volume of the liquid medium in the vessel makes up at least about 50% of the total volume of the vessel (including head space), in particular at least about 70%, more in particular at least about 85%. It may be preferred for the pressure at the end of the cyclic urea formation step is below about 15 bara, in particular below about 10 bara, in some embodiments below about 5 bara, or even below about 3 bara.

CO2-Transfer Step

In one embodiment the adduction step comprises a CO2 transfer step. In a CO2 transfer step, a carbonyl group is provided from a CO source to a starting compound comprising a —NH—CH2-CH2-NH— moiety or a —NH—CH2-CH2-OH moiety, or HO—CH2-CH2-OH in an adduction step providing a CO2 adduct of a starting compound comprising a —NH—CH2-CH2-NH— moiety or a —NH—CH2-CH2-OH moiety, or HO—CH2-CH2-OH. The CO sources have been discussed above.

Reaction conditions include a reaction temperature which generally is at least about 100° C. At a temperature below about 100° C., the reaction rate generally is too low to allow meaningful conversion within a reasonable time frame. It may be preferred for the reaction temperature to be at least about 125° C., in particular at least about 150° C., more in particular at least about 170° C. The reaction is generally carried out at a temperature of at most about 400° C. The temperature may thus be at most about 300° C., in particular at most about 250° C., or even at most about 220° C. Operating at a temperature of about 170-about 220° C. is considered preferred.

In general, the total pressure in the system is at most about 75 bara. The total pressure generally is at least about 2 bara, in particular at least about 5 bara, more in particular at least about 10 bara.

The amount of CO moieties provided to the reaction is not critical. The minimum amount is governed by the amount required to convert the starting material amine compound into its corresponding CO2 adduct. Therefore, the molar ratio between CO moieties and independent —NH—CH2-CH2-NH— moieties, —NH—CH2-CH2-OH moieties, or HO—CH2-CH2-OH generally is at least about 0.1:1. A ratio of at least about 0.2:1, in particular at least about 0.5:1 may be more attractive if more urea adduct is aimed for. A large excess of CO moieties is not detrimental to the process, but is generally less attractive for economic reasons. Therefore, as a general maximum a value of about 500:1 may be mentioned. The amount of CO moieties dosed will depend on the desired amount of urea adduct in the final product.

Reaction Step

In the reaction step of the process as contemplated herein a hydroxy-functional compound selected from the group of ethanolamines and dihydroxyethane with an ethyleneamine compound, wherein at least part of the total of hydroxy-functional compounds and ethyleneamine compounds is provided in the form of a CO2 adduct, to form CO2 adduct of a product polyethyleneamine compound.

The reaction step is preferably performed at a temperature of at least about 100° C. The temperature should preferably be lower than about 400° C. More preferably the temperature is between about 200 and about 360° C. Even more preferably the temperature is between about 230 and about 340° C. Most preferably the temperature is between about 250 and about 310° C. In embodiments where the ethanolamine-functional compound is monoethanolamine the most preferred temperature range is between about 230 and about 290° C.

The reaction time during the process is in an embodiment between about 5 minutes and about 15 hours, preferably between about 0.5 and about 10 hours, more preferably between about 1 and about 6 hours.

It will be clear to the skilled person that an overly long reaction time will be detrimental, not only for process-economical reasons, but also because it may lead to the formation of undesirable high-boiling side products. A too long reaction time can lead to undesirable degradation and color formation.

If any of the starting compounds contains piperazine units

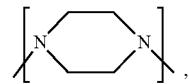

preferably the reaction is performed in a liquid wherein the liquid comprises water as then both the yield and selectivity can be increased. If one or more of the hydroxy-functional compound, ethyleneamine compound or carbon oxide delivering agent are liquid at the reaction conditions, these are not considered part of the above liquid in which the process of the disclosure is performed.

In a preferred embodiment when having compounds with piperazine units in the process of the disclosure, the liquid contains at least about 50 wt % of water up to about 100 wt % of water, wherein more preferably the remaining up to about 50 wt % is a polar liquid that mixes homogenously with water at the conditions employed during the process of the disclosure. Even more preferably the liquid contains at least about 75 wt-% of water, yet more preferably at least about 90 wt-%, most preferably at least about 95-wt % on total liquid weight.

The reactor employed can be any suitable reactor including continuously stirred tank reactor, pipeline reactor, tubular or multi-tubular reactor. The reactor may be adiabatic or equipped with external or internal heating devices. Feed may be single point or split into multiple points. It can consist of or include multiple stages with inter-stage heat exchange.

As will be clear to the skilled person, the apparatus used in the reaction step, but also in the various other steps of the process as contemplated herein, should be fit for purpose. That is, they should be able to withstand the long-time interaction with the reactants and products under reaction conditions, including, as described elsewhere, substantial temperatures and pressures. In addition to the reactor and other apparatus being able to withstand the reaction conditions, it is also important that they do no release material which would detrimentally affect the quality of the product produced. For example, as metal ions may result in color formation in the product, the material of construction for the various apparatus should be selected such that metal ions are not released to an unacceptable extent. Suitable materials include, but are not limited to, high quality steels such as austenitic stainless steels, super austenitic stainless steels, ferritic stainless steels, martensitic stainless steels, precipitation-hardening martensitic stainless steels, and Duplex stainless steels. It is within the scope of the skilled person to select suitable materials of construction.

The process can be carried out in one or multiple batch reactors, possibly in fed-batch operation, and/or in a continuously operating system in one reactor or in a cascade of continuous flow reactors, optionally with multiple feeding points.

It was found that when adding at least about 0.6 molar equivalents of carbon oxide delivering agent on ethyleneamine compound, the yield of ethyleneamines increases considerably and also the amount of side products decreases.

Hence it is preferred to have the molar ratio of CO2 and/or carbon oxide delivering agent to ethyleneamine compound at least about 0.6 to about 1.

Preferably, the molar amount of CO2 and/or carbon oxide delivering agents on ethyleneamine compounds is between about 0.7 and about 20 molar equivalents of carbon oxide delivering agent on moles of amine functional compound, and more preferably it is between about 0.7 and about 6:1, even more preferably between about 0.8:1 and about 3:1.

In another embodiment that leads to a high yield, the molar ratio of hydroxy-functional compound to ethyleneamine compound is at least about 0.7:1 and the molar ratio of carbon oxide delivering agent to ethyleneamine compound is at least about 0.05:1. In such embodiments the yield of ethyleneamines is also high.

Even more preferably the molar ratio of hydroxy-functional compound to ethyleneamine compound is between about 0.8 and about 5:1 and the molar ratio of carbon oxide delivering agent to amine functional compound is between about 0.2:1 and about 20:1.

Yet even more preferably the molar ratio of hydroxy-functional compound to ethyleneamine compound is between about 1:1 and about 2:1 and the molar ratio of carbon oxide delivering agent to ethyleneamine compound is between about 0.7:1 and about 3:1.

In one embodiment, to achieve a high selectivity of ethyleneamine on starting materials, especially on hydroxy-functional compound, the molar ratio of hydroxy-functional compound to ethyleneamine compound is preferably between about 0.05:1 and about 0.7:1 and the molar ratio of CO2 and/or carbon oxide delivering agent to ethyleneamine compound is higher than the molar ratio of hydroxy-functional compound to ethyleneamine compound.

More preferably the molar ratio of CO2 and/or carbon oxide delivering agent to ethyleneamine compound is at least about 10% higher than the molar ratio of hydroxy-functional compound to ethyleneamine compound. In another more preferred embodiment the molar ratio of hydroxy-functional compound to ethyleneamine compound is between about 0.1 and about 0.5.

It should be noted that carbon oxide delivering agents exist that contain more than one carbonyl group that can be released from the molecule for transfer to the hydroxy-functional compound, such as for example DU-TETA. When determining the molar ratio for such compounds there should be an adjustment for the molar amount of carbon oxide they can release for transfer to the hydroxyl-functional compound. Accordingly, about 1 mole of DU-TETA should be considered about 2 moles of carbon oxide delivering agent.

The molar ratio, as above, between compounds is determined by the reactants in the process, independent of the dosing regime used for the reactants.

Elimination Step

In the elimination step of the process as contemplated herein the $CO_2$ adduct of polyethyleneamine compound is converted to the corresponding polyethyleneamine compound. It is called an elimination step because the carbonyl group is eliminated from the molecule.

There are various ways to carry out the elimination step.

In one embodiment, the elimination step comprises the step of reacting the $CO_2$ adduct of polyethyleneamine compound with water to form $CO_2$ and the corresponding ethyleneamine compound. This embodiment is also indicated herein as a desorption step.

In another embodiment the elimination step is carried out by reacting the $CO_2$ adduct of polyethyleneamine compound with an inorganic base, resulting in the formation of a polyethyleneamine compound and a carbonate salt. This step is also indicated herein as a caustic treatment step. Within the context of the present disclosure, an inorganic base is a Lewis or Brøsted base which does not contain carbon-carbon bonds. In many embodiments the inorganic base contains a metal, alkali metal or alkaline earth metal cation, and in many embodiments it is a Brøsted base. Preferably the inorganic base is a strong inorganic base which is a base that does not contain carbon-carbon bonds and has a pKb of less than about 1.

In another embodiment, the elimination step is carried out by transferring the carbonyl group from the $CO_2$ adduct of the polyethyleneamine compound to a compound having a —NH—CH2-CH2-NH— moiety or a NH—CH2-CH2-OH moiety, or HO—CH2-CH2-OH. This step is also indicated as a $CO_2$ transfer step.

In one embodiment of the present disclosure, the elimination step comprises a first elimination step and a further elimination step, wherein the first elimination step and the further elimination step are independently selected from the group of a desorption step in which the $CO_2$ adduct of polyethyleneamine compound is reacted with water to form $CO_2$ and the corresponding polyethyleneamine compound, a caustic treatment step in which $CO_2$ adduct of polyethyleneamine compound is reacted with an inorganic base, resulting in the formation of a polyethyleneamine compound and a carbonate salt, and a $CO_2$ transfer step, wherein the carbonyl group from the $CO_2$ adduct of the polyethyleneamine compound is transferred to a compound having a —NH—CH2-CH2-NH— moiety or a NH—CH2-CH2-OH moiety, or HO—CH2-CH2-OH, wherein the first elimination step converts part of the CO2 adducts of polyethyleneamines present in the feed thereto into the polyethyleneamine compounds, while part of the CO2 adducts of polyethyleneamines present in the feed to the first elimination step is not converted in the first elimination step, and is provided to the second elimination step. Of course, provision of further elimination steps is also possible.

It may be preferred for the first elimination step to be a desorption step or a CO2 transfer step and the further elimination step to be a desorption step or a caustic treatment step, wherein the steps are not the same.

In one embodiment the elimination step comprises a desorption step in which not all CO2 adducts are converted to polyethyleneamine compounds. Thus, the product resulting from the desorption step may still comprise CO2 adducts of polyethyleneamine compounds. If this is the case, it has been found that the CO2 adducts are generally CO2 adducts of higher polyethyleneamine compounds rather than CO2 adducts of lower-boiling starting materials. In this case, if a separation step is carried out, it results in the separation of, in the first place, starting materials, in the second place, a product fraction of higher polyethyleneamine compounds and in the third place a fraction comprising CO2 adducts of higher polyethyleneamine compounds.

Desorption Step

In the desorption step carried out in one embodiment of the present disclosure, $CO_2$ adducts of ethyleneamine compounds are converted into ethyleneamine compounds by reaction with water, with removal of $CO_2$. The reaction takes place in the liquid phase.

The reaction with water generally takes place at a temperature of at least about 150° C. If the reaction temperature is below about 150° C., CO2 adducts of ethyleneamine compounds will not react to a significant extent. It is preferred for the reaction to be carried out at a temperature of at least about 180° C., in particular at least about 200° C., more in particular at least about 230° C., or even at least about 250° C. Preferably the temperature during this step does not exceed about 400° C., in particular at most about 350° C., more in particular at most about 320° C.

The pressure during the process is not critical, as long as the reaction medium is in the liquid phase. As a general range, a value of about 0.5 to about 100 bara may be mentioned, depending on the desired temperature. It is preferred for the CO2 removal step to be carried out at a pressure of at least about 5 bar, in particular at least about 10 bar, to maintain a sufficient amount of amine and water in the medium. In view of the high costs associated with high-pressure apparatus, it may be preferred for the pressure to be at most about 50 bar, in particular at most about 40 bar.

The amount of water depends on the desired degree of conversion and on the process conditions. In general, the amount of water is at least about 0.1 mole water per mole CO2 adduct moiety in the feedstock. Higher amounts are often used, e.g., at least about 0.2 mole per mole CO2 adduct moiety, in particular at least about 0.5 mole water per mole CO2 adduct moiety. The maximum is not critical for the process as contemplated herein but too large amounts of water will lead to unnecessarily large equipment being required. As a general maximum an amount of at most about 500 mole water per mole cyclic ethylene CO2 adduct moiety may be mentioned, in particular at most about 300 mole, more in particular at most about 200 mole, in some embodiments at most about 100 mole, or at most about 50 mole.

Depending on the reaction temperature and the desired degree of conversion, the reaction time can vary within wide ranges, e.g., at least one minute, in particular at least 5 minutes, more in particular between about 15 minutes and about 24 hours. In one embodiment, the reaction time may be at least about 30 minutes, or at least about 1 hour. It may be preferred for the reaction time to vary between about 1 hour and about 12 hours, in particular between about 1 hour and about 6 hours. When using lower temperatures, longer reaction times may be required to obtain the desired degree of conversion.

In one embodiment of the present disclosure, the desorption step is carried out by reacting CO2 adducts of ethyleneamine compounds in the liquid phase with water in an amount of about 0.1-about 20 mole water per mole CO2 adduct moiety, at a temperature of at least about 230° C., with removal of CO2. It has been found that the use of a low amount of water in combination with a relatively high temperature and CO2 removal results in an efficient process which good conversion and low formation of side products. It has been found that it is possible in this embodiment of the process as contemplated herein to obtain good conversion with the relatively limited amount of water of at most 20 mole water per mole CO2 adduct moiety. It has been found that it possible to work at even lower amounts of water, e.g., and amount of at most about 15 mole water per mole CO2 adduct moiety, more in particular an amount of at most about 10 mole water per mole CO2 adduct moiety, or even at most about 5 mole water per mole CO2 adduct moiety.

The range of about 0.1-about 20 mole water per mole CO2 adduct moiety refers to the entire amount of water added during the process, calculated on the amount of urea moieties in feedstock at the start of the reaction. To obtain full conversion, about 1 mole of water is required per mole CO2 adduct moiety to be converted. As full conversion is not always necessary, lower amounts of water may be possible. Therefore, water is used in an amount of at least about 0.1 mole per mole CO2 adduct moiety. Higher amounts are often used, e.g., at least about 0.2 mole per mole CO2 adduct moiety, in particular at least about 0.5 mole water per mole CO2 adduct moiety.

Water can be added at the beginning of the desorption step in a single dosing. It is preferred, however, to add the water during the process, in several dosings or continuously. In a continuous operation multiple feedpoints may be used. By matching the amount of water added to the amount of water consumed by the reaction, the excess water in the reaction mixture can be limited. It has been found that this limits the formation of side products.

The molar ratio of water to urea moieties is calculated on the water present in the liquid reaction medium. If water is added in the form of steam, which may be an attractive embodiment to combine water addition with the provision of heat to the reaction mixture, the majority of water in the steam will not be absorbed in the liquid reaction medium. It is within the scope of the skilled person to regulate the conditions of a water addition process via stream in such a way that the desired amount of water is absorbed by the reaction medium. The water can also be present in the feedstock from the beginning of the reaction, e.g., as a result of the process by which the feedstock was produced. Water can also be added as a liquid.

In one embodiment of the desorption step, CO2 is removed. CO2 removal can be carried out when the conversion of the ethyleneureas into ethyleneamine compounds has been completed. However, it is preferred to carry out CO2 removal during the reaction. CO2 removal can be carried out in manners known in the art. The most basic way to do this it to vent the reaction vessel. A stripping fluid, in particular a stripping gas can be used to increase CO2 removal rate. Other measures to improve removal of CO2 will be evident to the skilled person, and include measures like stirring of the reaction mixture, sparging of stripping gas, thin-film evaporation, use of packing or trays, etc.

Where a stripping gas is used, the flow rate is typically at least about 1 m$^3$ per about 1 m$^3$ reactor volume per hour (at reaction temperature and pressure), and at most about 100 m$^3$ per about 1 m$^3$ reactor volume per hour (at reaction temperature and pressure). The stripping flow rate can be generated by evaporation of a liquid inside the reactor vessel, resulting in in situ generation of stripping gas. The ranges above also apply to this embodiment. Of course, it is also possible to combine the addition of stripping gas with the in situ formation of stripping gas.

The CO2-containing stripping fluid removed from the CO2 removal step can, for example, comprise from about 1 to about 99 mol. % CO2. In other embodiments, the stripping fluid may comprise about 1-about 80 mol. % CO2, or about 1-about 60 mol. % CO2. In some embodiments, the effluent from the CO2 removal step may comprise about 1-about 40 mol. % CO2, or about 1-about 20 mol. % CO2. Lower CO2 contents make for more efficient stripping, but also for the use of more stripping gas. It is within the scope of the skilled person to find an appropriate balance between these parameters.

If so desired the desorption step can be carried out with water in the presence of an amine compound selected from the group of primary amines, cyclic secondary amines, and bicyclic tertiary amines.

Primary amines are amine functional compounds in which the amine group is of the formula R4-NH2 and wherein R4 can be any organic group, preferably an aliphatic hydrocarbon with optional heteroatoms such as oxygen and/or nitrogen. Secondary cyclic amines are amines of the formula R5-NH—R6, wherein R5 and R6 together form a hydrocarbon ring, optionally with heteroatoms such as oxygen and/or nitrogen, preferably a piperazine ring. Tertiary bicyclic amines are amines of the formula R7-N(—R9)-R8 where R7 and R8 together form a hydrocarbon ring—optionally with heteroatoms such as oxygen and/or nitrogen—and R7 and R9 together form another hydrocarbon ring—optionally with heteroatoms such as oxygen and/or nitrogen. On all the above groups R4 to R9 substituents can be present, like alkyl or hydroxyalkyl groups. Primary amines, cyclic secondary amine and bicyclic tertiary amines all contain a sterically relatively unhindered amine group. In this document a compound is defined as a primary amine or a secondary cyclic amine or a tertiary bicyclic amine if one of the amine groups in the compound is a primary amine or secondary cyclic amine or a tertiary bicyclic amine group, independent of if this compound contains further amine groups that may be different in their nature. A compound can also contain two or more different amine functionalities, e.g. a primary amine and a secondary cyclic amine functionality or a primary amine, a secondary cyclic amine and a tertiary bicyclic amine functionality.

Preferred examples of primary amines are alkylamines, linear ethyleneamines, and alkanolamines Preferred examples of cyclic secondary amines are amines that contain a terminal piperazine ring. Preferred examples of bicyclic tertiary amines are 1,4-diazabicyclo[2.2.2]octane (DABCO), 1,4-diazabicyclo[2.2.2]octan-2-yl)methanol and 1-azabicyclo[2.2.2]octane (Quinuclidine).

The amine compound is preferably a compound with more than one amine group wherein at least one of the amine groups is a primary amine, even more preferably it is an amine wherein two amine groups are a primary amine Preferred amine compounds include ethylenediamine (EDA), N-methylethylenediamine (MeEDA), diethylenetriamine (DETA), ethanolamine (MEA), aminoethylethanolamine (AEEA), piperazine (PIP), N-aminoethylpiperazine (AEP), 1,4-diazabicyclo[2.2.2]octane (DABCO), 1,4-diazabicyclo[2.2.2]octan-2-yl)methanol, triethylenetetramine (TETA), N-diethyldiamine-2-imidazolidinone (U1TETA), N, N'-diaminoethylpiperazine (DAEP), N, N'-diaminoethyl-2-imidazolidinone (U2TETA), tetraethylenepentamine (TEPA), pentaethylenehexamine (PEHA), and the mono cyclic ureas of TEPA and PEHA (i.e. U1TEPA, U2TEPA, U1PEHA, U2PEHA, U3PEHA) and the dicyclic urea isomers of PEHA (i.e. DUPEHA), a polyethyleneimine (PEI) or an ethyleneamine on a solid carrier.

The amine compound is preferably present in a molar amount of between about 0.001 and about 100 equivalents per mole CO2 adduct moiety, more preferably between about 0.01 and about 50 equivalents, even more preferably between about 0.05 and about 30 equivalents, yet more preferably between about 0.15 and about 25 equivalent and most preferably between about 0.20 and about 20 equivalents.

In the desorption step, CO2 adducts of ethyleneamine compounds are converted to CO2 and ethyleneamine compounds. It is preferred for at least about 10 mole % of the CO2 adduct moieties in the system to be converted to the corresponding ethyleneamine moieties. The maximum will depend on the following desorption and recycle steps.

Treatment with (Strong) Inorganic Base

In one embodiment, an elimination step is carried out using a (strong) inorganic base. Within the context of the present disclosure, a strong inorganic base is a base with a material which does not contain carbon-carbon bonds and which has a pKb of less than about 1.

In one embodiment, the strong inorganic base is selected from the group of metal hydroxides, in particular from the group of hydroxides of alkaline and earth alkaline metals, in particular from sodium hydroxide, potassium hydroxide, lithium hydroxide, calcium hydroxide, magnesium hydroxide, and barium hydroxide. In one embodiment, the strong inorganic base is selected from the group of metal oxides, in particular from the group of oxides of alkaline and earth alkaline metals, in particular from calcium oxide, magnesium oxide, and barium oxide. Selecting a strong inorganic base from the group of sodium hydroxide, potassium hydroxide, magnesium (hydr)oxide, and calcium (hydr)oxide may be preferred. The use of sodium hydroxide and potassium hydroxide may be particularly considered preferred. Other strong inorganic bases may also be used, such as ammonium hydroxide. As will be evident to the skilled person, mixtures of various inorganic bases can be used. Compounds comprising a base in addition to other components can also be used, as can be compounds which will be converted into inorganic bases in the reaction medium.

The lower limit of the molar ratio of inorganic base to CO2 adduct moieties is not critical. A value of at least about 0.2:1 may be mentioned. If it is desired to obtain full conversion of the CO2 adduct moieties into the corresponding ethyleneamine compound, the use of larger amounts may be preferred, e.g., in a molar ratio of at least about 0.5:1, in particular at least about 1:1. It may be preferred to use larger amounts to increase the reaction rate, e.g., a molar ratio of inorganic base to CO2 adduct moiety of at least about 1.5:1, in particular at least about 2:1.

As large amounts of base do not contribute to further conversion but will lead to additional costs, it is preferred for the molar ratio of the inorganic base to the molar amount of $CO_2$ adduct moieties in the product provided to the treatment with the inorganic base to be at most about 20:1, in particular at most about 15:1, more in particular at most about 10:1. It has been found that even lower amounts of inorganic base can suffice, in contrast to what has been disclosed in the prior art. More in particular, it has been found that good results can be obtained at a molar ratio of inorganic base to $CO_2$ adduct moieties of at most about 7.5:1, in particular at most about 6.5:1, even more in particular at most about 5.5:1. It has been found that the use of a molar ratio of at most about 5.5:1 results in full conversion of the $CO_2$ adduct moieties and high yield of the resulting ethyleneamine compounds. It may be preferred to use even less inorganic base per mole of $CO_2$ adduct moiety, e.g., in a more ratio of at most about 5:1, in particular at most about 4:1, more in particular at most about 3:1. The molar ratio is calculated on the molar amount of $CO_2$ adduct moieties in the feed provided to the caustic treatment step.

The treatment with inorganic base can, for example, be carried out by contacting the material to be treated with a concentrated aqueous solution of the inorganic base. Depending on the nature of the base and the further composition of the reaction mixture, it may also be possible to add the base in solid form and dissolve it in the reaction medium. As will be clear to the skilled person, the aim is to bring the base in a dissolved state, so that the hydroxy groups can react with the $CO_2$ adduct, while avoiding unnecessary dilution of the reaction medium.

The reaction can be carried out at a temperature between room temperature and about 400° C. The temperature and pressure should be selected such that the reaction mixture is in the liquid phase. Higher temperatures are advantageous because they lead to decreased reaction times. It may be preferred to carry out the reaction at a temperature of at least about 100° C., in particular at least about 140° C., in particular at least about 170° C. On the other hand, higher temperatures may lead to the undesired formation of side products. It may therefore be preferred to carry out the reaction at a temperature of at most about 350° C., in particular at most about 280° C.

Depending on the reaction temperature, the reaction time can vary within wide ranges, e.g., between about 15 minutes and about 24 hours. It may be preferred for the reaction time to vary between about 1 hour and about 12 hours, in particular between about 1 hour and about 6 hours. When using lower amounts of base, longer reaction times may be required to obtain the desired degree of conversion.

In one embodiment, as discussed elsewhere herein, the caustic treatment step from the second reaction sequence may be combined with a caustic treatment elimination step from the first reaction sequence. In that case, as the conversion of the $CO_2$ adduct of the ethyleneamine compound into the corresponding ethyleneamine compound, requires more stringent conditions than the conversion of the ethyleneamine hydrohalide salt into ethyleneamine Therefore, if the two reactions are to be combined in a single step, the conditions and the amount of base should be selected such that both reactions take place. The conditions described above for the conversion of the $CO_2$ adduct of the ethyleneamine into the corresponding ethyleneamine should suffice.

Upon completion of the reaction, a reaction mixture will be obtained which contains ethyleneamine compounds and a carbonate salt of the inorganic base. The salt can be removed by methods known in the art, e.g., by filtration where the salt is in solid form.

The process as contemplated herein can be carried out in batch operation, fed-batch operation, or in a continuous operation, e.g., in a cascade of continuous flow reactor. Depending on the scale of the operation, continuous operation may be preferred.

Combination of Elimination Steps

A particular combination of elimination steps include a desorption step followed by a treatment with strong inorganic base, optionally after a separation step in which desired compounds have been removed.

In one embodiment, this combination encompasses the conversion of cyclic ethyleneureas into their corresponding ethyleneamines by a process comprising
in a first step converting cyclic ethyleneureas into their corresponding ethyleneamines by reacting cyclic ethyleneureas in the liquid phase with water with removal of $CO_2$, so as to convert between about 5 mole % and about 95 mole % of ethyleneurea moieties in the feedstock to the corresponding amines, and
in a second step adding a inorganic base and reacting cyclic ethylene ureas remaining from the first step with the inorganic base to convert them completely or partially into their corresponding ethyleneamines Another particular combination of elimination steps include a combination of one or more desorption steps with one or more reactive separation steps. The reactive separation encompasses $CO_2$ transfer wherein the carbonyl group from the $CO_2$ adduct of the product polyethyleneamine compound is transferred to a compound having a —NH—CH2-CH2-NH— moiety or a NH—CH2-CH2-OH moiety, or HO—CH2-CH2-OH.

In one embodiment this combination encompasses the conversion of a feedstock comprising cyclic ethyleneureas into their corresponding ethyleneamines, by a process comprising
a desorption step in which cyclic ethyleneureas are converted into their corresponding ethyleneamines by reacting cyclic ethyleneureas in the liquid phase with water with removal of $CO_2$,
a reactive separation step wherein cyclic ethyleneureas are converted into their corresponding ethyleneamines by reaction with an amine compound selected from the group of primary amines or secondary amines which have a higher boiling point than the ethyleneamines formed during the process.

The reactive separation step may preferably be carried out as a reactive distillation step. This embodiment is also discussed above in the context of the reaction step.

In one embodiment the desorption step precedes the reactive separation step. In another embodiment, the reactive separation step precedes the desorption step. It is also possible to perform at least two desorption steps, with one or more reactive separation step being performed in between, or at least two reactive separation steps, with one or more reactive desorption steps being performed inbetween.

The reactive separation step may be conducted at any suitable pressure. During the reaction, the pressure in the reactive separation system preferably is at most about 127 bara, more preferably at most about 50 bara, and even more preferably at most about 25 bara. Depending on the composition of the reaction medium, lower pressures may be applied, e.g., less than about 15 bar, or less than about 5 bar. The process can also be carried out at a pressure below atmospheric pressure, such as less than about 700 mbara, more preferably below about 100 mbara, even more preferably below about 25 mbara, and most preferably below about 5 mbara. In general the pressure will be at least about 0.1 mbara.

The reactive separation step is preferably carried out at a temperature of at least about 150° C., in particular at least about 180° C., in some embodiments at least about 200° C., or at least about 230° C., sometimes at least about 250° C. Preferably the temperature during the process does not exceed about 400° C., more preferably about 350° C. In one embodiment, the reactive separation step amine removal step is carried out at a temperature in the range of about 180-about 300° C. and a pressure of at most about 2000 mbara, in particular at most about 1000 mbara, more in particular at most about 500 mbara, more in particular at most about 200 mbara. It may be preferred to carry out the reactive separation step at a temperature of about 200-about 260° C. and a pressure of at most about 50 mbara. The reactive separation step generally is performed for a time of between about 1 minute and about 12 hours. Preferably the reactive separation step is run in less than about 10 hours, more preferably in less than about 8 hours, most preferably less than about 5 hours.

In some embodiments it is favorable to at least partially combine the reaction step with the separation, and/or elimination step by performing a reactive separation step, such as a reactive distillation. In a reactive separation step the above reaction step finds place under conditions selected such that the CO2 adduct of the starting compounds reacts to give CO2 adduct of product polyethyleneamine and in the same reactive separation the formed CO2 adduct of product polyethyleneamine is either separated from other components, or transfers it CO moiety to another component in the reactor, which can be either remaining starting compounds or byproducts.

In one embodiment CO2 adducts of ethyleneamine compounds are converted into their corresponding ethyleneamine compounds by reaction with an amine compound chosen from the group of primary amines or secondary amines that have a higher boiling point than the ethyleneamine compounds formed during the process, wherein the process is a reactive separation process and the reaction mixture contains less than about 10 wt % of water on the basis of total weight of the reaction mixture. It may be preferred to carry out the reaction in less than about 7 wt % of water on total reaction mixture. It may be preferred for the pressure to be less than about 25 bara, in particular less than about 500 mbara. In general, the reaction will be done at a temperature of at least about 150° C.

The Second Reaction Sequence

The second reaction sequence comprises the steps of
in an amination step reacting monoethanolamine with ammonia in the presence of hydrogen and an amination catalyst to form a reaction mixture comprising ethylenediamine,
in a separation step separating the reaction mixture derived from the amination step into at least two fractions.

In the process of the present disclosure at least one amination step takes place.

The reaction of a compound comprising a hydroxyl-group with a compound selected from ammonia and compounds comprising an amine group may be indicated as a reductive amination reaction. The transfer of an amino group from one molecule to another, or within the same molecule may be indicated as a transamination reaction. As will be evident to the skilled person, in a reactor containing a compound comprising a hydroxyl-group, e.g., monoethanolamine, and compounds comprising amino groups both reductive amination reactions and transamination reactions will take place. Therefore, in the present specification the term amination step will be used. The term transamination will only be used for the specific situation that compounds comprising a hydroxyl-group are not present in the system.

The second reaction sequence comprises an amination step in which monoethanolamine is reacted with ammonia in the presence of hydrogen in the presence of an amination catalyst to form a reaction mixture comprising ethylenediamine The reaction mixture provided to the reaction may comprise further components, such as hydroxyl-functional compounds such as aminoethylethanolamine (AEEA), hydroxyethyldiethylenetriamine (HE-DEATA), diethanolamine (DEA), and hydroxyethyl-triethylenetetramine (HE-TETA), and ethyleneamine compounds such as N-methylethylenediamine (MeEDA), diethylenetriamine (DETA), piperazine (PIP), N-aminoethylpiperazine (AEP), triethylene tetramine (TETA), N, N'-diaminoethylpiperazine (DAEP), tetraethylenepentamine (TEPA), and pentaethylenehexamine (PEHA). These compounds can be provided from external sources, but also as recycle streams from other steps from the second and first reaction sequences.

The second reaction sequence can also comprise one or more further amination steps. In one embodiment, the second reaction sequence comprises at least one further amination step wherein an ethyleneamine reactant is reacted with compound selected from ammonia or a further ethyleneamine reactant in the presence of hydrogen and an amination catalyst. In this embodiment, the ethyleneamine reactant may be selected from the group of hydroxyl-functional compounds and amine-functional compounds as stated above. Specific embodiments of further amination steps comprise:
an amination step wherein EDA is reacted to form higher ethyleneamines
an amination step wherein EDA is reacted with MEA to form higher ethyleneamines As will be evident to the skilled person, in all cited steps further compounds may also be present, and appropriate recycles may be applied.

In one embodiment, the process as contemplated herein encompasses at least two amination steps wherein in the first amination step monoethanolamine is reacted with ammonia, to form ethylenediamine and further compounds, and in a second amination step ethylenediamine is reacted in the presence of hydrogen and a catalyst to form higher ethyleneamines, wherein higher ethyleneamines are defined as ethyleneamines which contain more ethylene moieties than ethylenediamine. Of course, some higher ethyleneamines will also be formed in the first amination step.

In one embodiment, EDA from the first amination step is provided as starting material to the second amination step. The product from the second amination step can be provided to the separation step. While it is possible to provide the entire effluent from the first amination step to the second step, it may be preferred to carry out an intermediate separation step, and provide in particular EDA to the second amination step. It is possible to provide MEA to the second amination step, but this is an optional embodiment.

Where the amination reaction encompasses the reaction of an ethanolamine such as monoethanolamine or aminoethylethanolamine with ammonia, the reaction is generally carried out at a temperature in the range of about 120-about 225° C. Ammonia is generally added in an excess amount of at least about 3 moles per mole ethanolamine, in particular at least about 5 moles per mole ethanolamine, more in particular at least 10 moles per mole ethanolamine Pressure is generally in the range of about 5-about 30 MPa, in particular about 10-about 20 MPa.

Where ammonia is not present in the amination reaction, the reaction is generally carried out at a temperature in the range of about 130-about 200° C., in particular in the range of about 140-about 180° C. The pressure is generally in the range of about 5 to about 40 MPa, more in particular in the range of about 10 to about 20 MPa.

Catalysts suitable for use in amination are known in the art. Suitable catalysts include catalysts comprising at least one metal component on a porous inorganic carrier. Examples of metal components are nickel, rhenium, cobalt, iron, copper, platinum and palladium. The use of nickel-based catalysts is known to be attractive in amination processes. It is within the scope of the skilled person to select a suitable amination catalyst and process conditions.

Conversion of Ethyleneoxide and Ammonia to Monoethanolamine

In one embodiment of the present disclosure, a step of manufacturing monoethanolamine from ethyleneoxide and ammonia is present in the process as contemplated herein. This ethyleneoxide conversion step can be present in the second reaction sequence to manufacture the monoethanolamine provided to the amination step. It can also be present in the first reaction sequence to provide monoethanolamine to the adduction step or the chain extension step. In a preferred embodiment of the disclosure, monoethanolamine derived from the ethyleneoxide conversion step is provided to both the first reaction sequence and the second reaction sequence, as this makes it possible to use the widely available starting materials ethyleneoxide and ammonia to manufacture a wide variety of products.

The reaction of ethyleneoxide and ammonia may generate dihydroxyethyleneamine (DEA) as side product. In one embodiment of the present disclosure, DEA generated in the ethyleneoxide conversion step is provided to the adduction step or the chain extension step of the first reaction sequence, where it can serve as a starting material for reaction with an ethyleneamine compound, to manufacture higher ethyleneamines The reaction of ethyleneoxide and ammonia to form monoethanolamine is known in the art. In general, ethyleneoxide and ammonia are reacted in the condensed phase at a temperature of about 20-about 250° C., with a pressure sufficient to keep the components in the condensed phase Ammonia will generally be provided in an excess, with the molar ratio of ammonia to ethyleneoxide being, e.g., in the range of about 10:1 to about 80:1. Ammonia may be provided in anhydrous form, or in an aqueous solution. In one embodiment, especially where ammonia is provided in anhydrous form, an acid catalyst, in particular a solid acid catalyst may be present. As processes for manufacturing monoethanolamine from ethyleneoxide and ammonia are known in the art, it requires no further elucidation here.

Connection of the First and Second Reaction Sequences

In the process as contemplated herein, the first reaction sequence and the second reaction sequence are connected in that at least one of the following takes place:
  effluent from a step in the first reaction sequence is provided as starting material to a step in the second reaction sequence,
  effluent from a step in the second reaction sequence is provided as starting material to a step in the first reaction sequence,
  a step from the first reaction sequence and a step from the second reaction sequence are combined, or
  effluent from a step in the first reaction sequence is combined with effluent from a step in the second reaction sequence.

There are numerous ways in which the first reaction sequence and the second reaction sequence can be connected.

In one embodiment of the present disclosure product from the amination step in the second reaction sequence is provided to the adduction step or the reaction step in the first reaction sequence, directly, or with an intermediate separation step being carried out.

This embodiment is considered advantageous because it allows the use of low-molecular weight ethyleneamine compound fractions generated in the second reaction sequence, e.g., AEEA, PIP, DETA, and EDA, to be used as starting material in the manufacture of higher molecular weight ethyleneamine compounds through the process of the first reaction sequence.

This embodiment may be particularly advantageous where EDA, DETA, and/or AEEA produced in amination step is provided to the adduction step or chain extension reaction step. In the case of EDA the process can be carried out with MEA and ammonia as starting materials for the second reaction sequence and MEA and EDA, the latter derived from the second reaction sequence, as starting materials for the first reaction sequence. This makes it possible to prepare a wide variety products from widely available and inexpensive starting materials. This embodiment combines the advantages of the two reaction sequences, in that the first reaction sequence makes it possible to obtain higher ethyleneamine products, but is less effective in doing so starting from ammonia, while the second reaction sequence can use the combination of MEA and ammonia as starting material, but has been found to be less selective when the aim is to manufacture higher ethyleneamine products.

Figure 2:
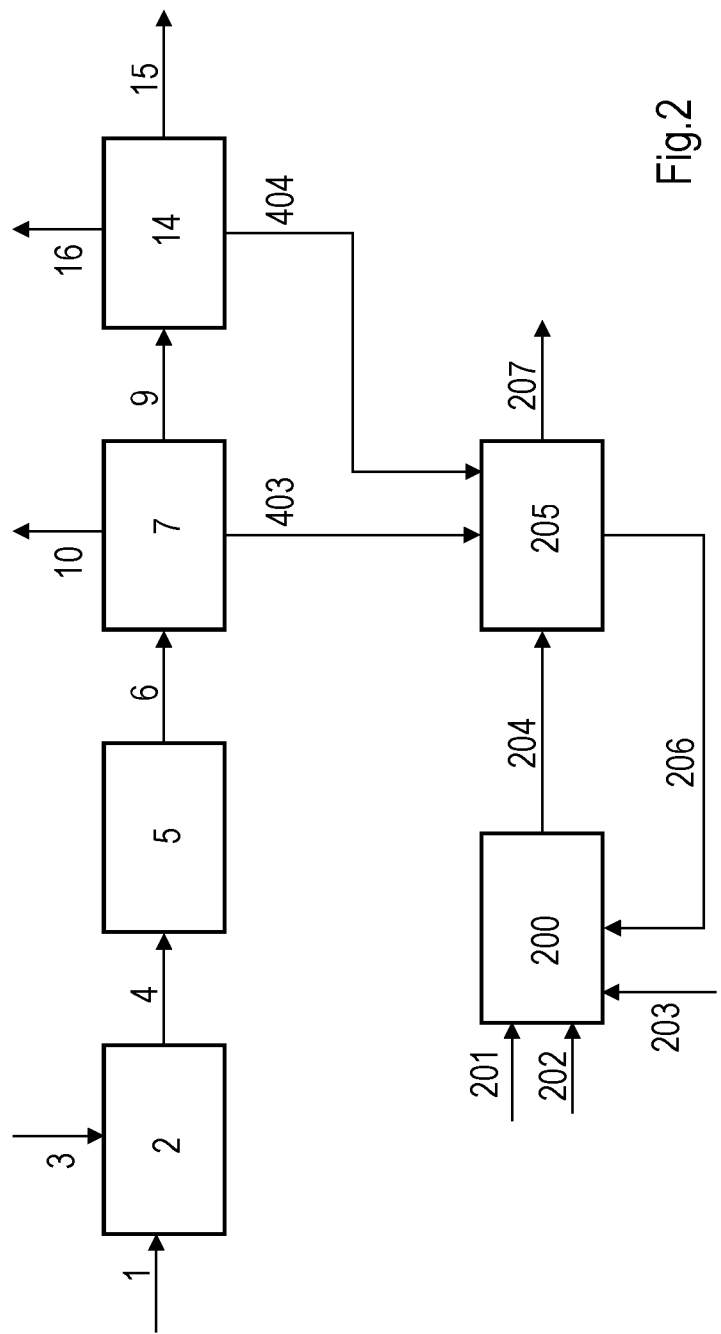
FIG. 2 illustrates further embodiments of the process as contemplated herein.
Figure 2A:
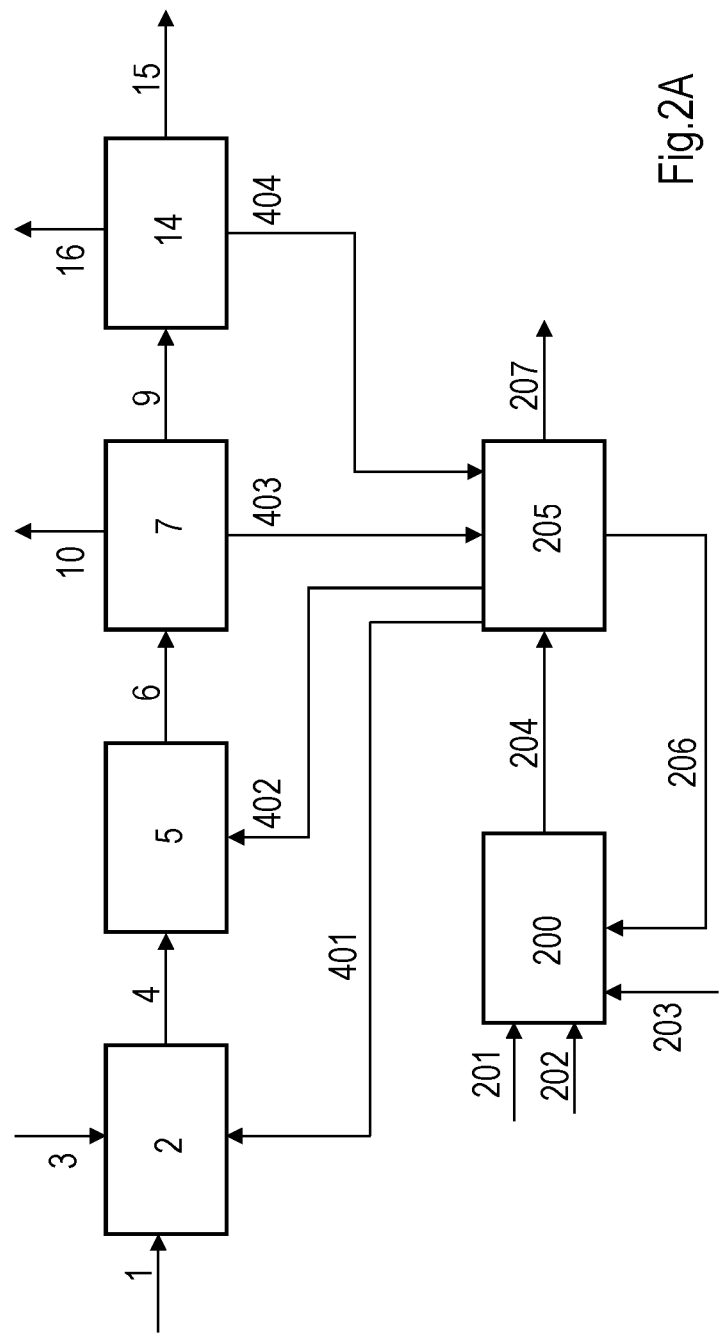
FIG. 2a illustrates further embodiments of the process as contemplated herein.

Additionally, connecting the two reaction sequences in this manner makes it possible to obtain increased product slate flexibility by allowing shifting the output from products which are less in demand to products which are more in demand One way of performing this embodiment is illustrated in FIG. 1 and FIG. 2A. A variation on this embodiment is described in FIG. 5.

In one embodiment of the present disclosure product from the amination step and product from the elimination step are combined and provided to a separation step. Various ways of combining the separation steps may be envisaged, ranging from combining the entire product of both reaction sequences. combining the entirety of the product of one reaction sequence with part of the product of the other reaction sequence, and combining part of the product of one reaction sequence with part of the product from another reaction sequence. In general, combining separation steps makes for increased efficiency from an operating point of view, both as regards apparatus costs and as regards operating costs. One way of performing this embodiment is illustrated in FIG. 2. Another way of performing this embodiment is in FIG. 3. In general, combining separation steps may be efficient from a cost point of view, while keeping them separate allows the separation being carried out under optimized conditions, which may allow process efficiency.

Figure 2B:
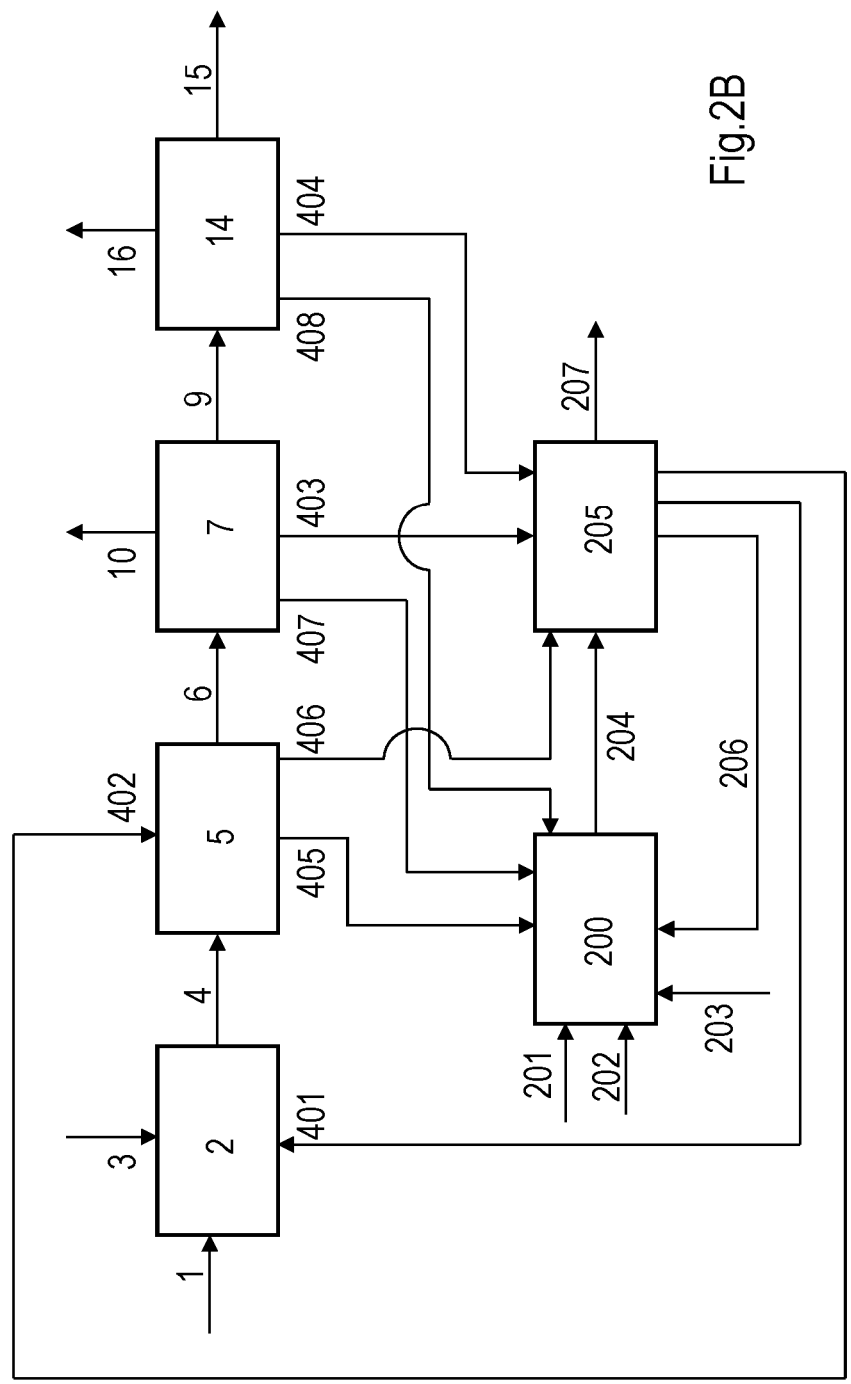
FIG. 2b illustrates further embodiments of the process as contemplated herein.

In one embodiment product from the chain elongation step of the first reaction sequence is provided to one or more of the amination reaction step and the separation step of the second reaction sequence. This is advantageous because it allows increased process flexibility, which is attractive for reasons given above. One way of carrying out this embodiment is illustrated in FIG. 2B (lines 405, 406, respectively).

In one embodiment the product from the elimination step or, where present, separating step from the first reaction sequence is provided to the amination reaction. Again, this is advantageous because it allows increased process flexibility, which is attractive for reasons given above. One way of carrying out this embodiment is illustrated in FIG. 2B (lines 407, 408, respectively).

In one embodiment of the present disclosure the elimination step in the first reaction sequence encompasses a distillation step, and product from the amination step is provided to the distillation step in the elimination step. This embodiments allows the combination of various separation steps into a single unit. This make for more efficient operation and reduction of CAPEX and OPEX.

In one embodiment of the present disclosure, the second reaction sequence comprises at least one further amination step wherein an ethyleneamine reactant is reacted with compound selected from ammonia or a further ethyleneamine reactant in the presence of hydrogen and an amination catalyst.

In particular the further amination step encompasses a step selected from an amination step wherein EDA is reacted to form higher ethyleneamines and an amination step wherein EDA is reacted with MEA to form higher ethyleneamines A preferred embodiment of the process as contemplated herein is one in the second reaction sequence encompasses at least two amination steps wherein in the first amination step monoethanolamine is reacted with ammonia, to form ethylenediamine, and in a second amination step ethylenediamine is reacted in the presence of hydrogen and an amination catalyst to form higher ethyleneamines, wherein higher ethyleneamines are defined as ethyleneamines which contain more ethylene moieties than ethylenediamine In one embodiment of the present disclosure product from a further amination step in the second reaction sequence and product from the elimination step in the first reaction sequence are combined and provided to a separation step. This embodiments allows the combination of various separation steps into a single unit. This make for more efficient operation and reduction of CAPEX and OPEX.

In one embodiment of the present product from the first reaction sequence and product from the second reaction sequence are provided to a single purification step. Combining these steps makes for a more efficient use of apparatus, with associated reduction of costs.

In one embodiment, the process further comprises an ethyleneoxide conversion step wherein ethyleneoxide and ammonia are reacted to produce monoethanolamine, and the monoethanolamine is provided to one or more of the amination step, the adduction step, or the chain extension reaction step. The use of monoethanolamine derived from the reaction of ethyleneoxide and ammonia makes for the use of inexpensive widely available starting materials and the presently claimed process is a flexible way of making use of this material. In this way it is possible to obtain higher ethyleneamines from ethyleneoxide and ammonia, without the necessity of providing further EDA compounds. In one embodiment, the process of the present disclosure comprises the step of reacting ethyleneoxide and ammonia to form monoethanolamine, wherein a first part of the monoethanolamine is provided to the amination step in the second reaction sequence where it is reacted with ammonia to form EDA, which EDA is provided at least in part to the adduction step or the chain-extension step of the first reaction sequence, and wherein a second part of the monoethanolamine is provided to the adduction step or the chain-extension step of the first reaction sequence. This embodiment makes it possible to derive all ethyleneamine and ethanolamine starting materials from ammonia and ethyleneoxide, without the addition of ethyleneamine or ethanolamine compounds from other sources being required.

The figures of the present application show various manners in which this can be effected. It will be evident to the skilled person that various manners of connecting the sequences can be combined, even if they are provided in different figures.

The disclosure will be illustrated with reference to the following figures, without being limited thereto or thereby. For all processes and figures present herein the following applies.

Intermediate separation steps may be present, also if they are not specified or shown.

Effluents from process steps can be provided to other process steps in part or in their entirety, whether or not after an intermediate separation step has been carried out.

Appropriate recycle of starting materials or intermediate products may be carried out, also if it is not specified or shown.

Purge streams and make-up streams may be present, also if they are not specified or shown.

Reactants may be provided individually or in combination, also if this is not specified or shown.

The different steps in the Figures do not necessarily refer to different units or reactors.

Embodiments of the present disclosure may be combined, unless they are mutually exclusive.

Elements of the figures can be combined, and as will be evident from the description, not all elements shown are essential to a specific embodiment.

Sometimes reaction streams are indicated with the shorthand wording ethyleneamine compound. This wording should not be interpreted as limiting on the content of the fraction, which, as will be evident to the skilled person, may contain other compounds also, e.g., if present, ethanolamine compounds, or, if present, CO adducts of ethyleneamine or ethanolamine compounds.

FIG. 1 illustrates a first embodiment of the present disclosure, in which the two reaction sequences are connected in that effluent from a step in the second reaction sequence is provided to a step in the first reaction sequence.

In FIG. 1, a starting compound comprising a —NH—CH2-CH2-NH— moiety or a —NH—CH2-CH2-OH moiety, or HO—CH2-CH2-OH is provided through line 1 to adduction step 2, where a carbon oxide delivering agent, e.g., CO2 or another carbon ode delivering agent is added through line 3. Of course, the CO adduct can also be provided in other manners, as described herein, e.g., through CO transfer. The adduct is provided to a chain-extension reaction step 5 through line 4. Additional reactants can be provided to chain-extension reaction step 5 through lines not shown. For example, if the product from the adduction step is an CO2 adduct of an ethyleneamine compound, an ethanolamine compound can be provided to chain-extension reaction step 5. The effluent from the chain-extension reaction step 5 is provided to elimination step 7 through line 6. In the CO2 elimination step 7, CO2 adduct of ethyleneamine compound is converted to the corresponding ethyleneamine compound, which is withdrawn through line 9. The compound comprising the carbonyl group eliminated from the CO2 adduct of the product ethyleneamine compound is withdrawn through line 10. While not essential to the present disclosure, FIG. 1 also contains a separation step 14, which is provided after the elimination step 7. The separation step 14 results in the separation of different fractions. For example, starting materials and/or intermediate compounds can be withdrawn through line 16. They can, if so desired be provided to adduction step 2 and/or chain-extension reaction step 5 through lines not shown. Separation step 14 also yields a product fraction of higher ethyleneamine compounds which is withdrawn through line 15. This part of the figure thus illustrates the first reaction sequence.

In the second reaction sequence, monoethanolamine is provided to an amination reaction step 200 through line 201. Ammonia is provided through line 202, and hydrogen may be provided through line 203. The product mixture from the amination reaction 200 is provided through line 204 to a separation step 205. The separation step yields at least two fractions. In the embodiment illustrated in this figure, a recycle stream 206 recycles ammonia and optionally hydrogen to the amination reactor 200. A product stream comprising ethyleneamines is withdrawn from the process through line 207. The separation step 205 may yield more fractions than the two which are specified here. All fractions may be processed as desired. For example, product fraction 207 may be submitted to further separation or purification steps not shown. The same goes for other fractions. Line 401 provides a fraction comprising ethyleneamine or ethanolamine compounds having a —NH—CH2-CH2-NH— moiety or a —NH—CH2-CH2-OH moiety to the adduction step 2. Examples of suitable compounds are in particular monoethanolamine and ethylenediamine, but higher molecular weight compounds may also be provided. Line 402 provides a fraction comprising ethyleneamine or ethanolamine compounds to the chain extension step 6. The composition of the two fractions in lines 401 and 402 may be the same or different, and it will be clear to the skilled person that it is also possible to have only one of fractions 401 and 402. In one embodiment this fraction comprises cyclic compounds such as piperazine or aminoethylpiperazine which, upon further processing in the first reaction sequence can result in the formation of higher ethyleneamine compounds containing piperazine rings, e.g., piperazinoethyl ethylenediamine (PEEDA), diaminoethylpiperazine, and the piperazine-ring-containing penta- and hexaethyleneamines.

The embodiment of FIG. 1 is considered advantageous because it allows the use of low-molecular weight ethyleneamine compound fractions generated in the second reaction sequence, e.g., AEEA, PIP, DETA, and EDA, to be used as starting material in the manufacture of higher molecular weight ethyleneamine compounds through the process of the first reaction sequence.

This embodiment may be particularly advantageous where EDA produced in amination step 200 is provided to adduction step 2 or chain extension reaction step 5. In that case the process can be carried out with MEA and ammonia as starting materials for the second reaction sequence and MEA and EDA, the latter derived from the second reaction sequence, as starting materials for the first reaction sequence. This makes it possible to prepare a wide variety products from widely available and inexpensive starting materials. A variation on this embodiment is described in FIG. 5.

FIG. 2 illustrates a second embodiment of the present disclosure, in which the two reaction sequences are connected in that effluent from a step in the first reaction sequence is provided to a step in the second reaction sequence.

FIG. 2 shows the same entities as FIG. 1. However, instead of lines 401 and 402 present in FIG. 1, in FIG. 2 a fraction is withdrawn from elimination step 7, through line 403 and provided to separation step 205. A fraction from separation step 404 of the first reaction sequence can be provided to separation step 205 of the second reaction sequence through line 404. it will be clear to the skilled person that it is also possible to have only one of fractions 403 and 404.

This embodiment allows efficient and cost-effective tailoring of the separation steps. Further, this process allows the provision of compounds, in particular low-molecular weight compounds such as MEA, EDA, DETA, AEEA, and PIP, which may be present in the reaction mixture of the reaction formed in the first reaction sequence to be processed in an efficient manner in the second reaction sequence. In FIG. 2 these fractions are provided to the separation step 205 through line 404, where they may be part of the recycle fraction provided to the amination step 200 through line 206. It is also possible to provide a fraction originating from separation step 14 to amination step 200 through lines not shown.

FIG. 2A illustrates a preferred embodiment of the present disclosure, in which all of lines 401, 402, 403, and 404 are presented. This figure thus is an illustration of a preferred embodiment of the present disclosure in which with the first reaction sequence and the second reaction sequence are connected in that:

ethyleneamine produced in the second reaction sequence is provided to the absorption step and/or the chain extension step in the first reaction sequence, and ethyleneamine product from the salt separation step in the second reaction sequence is provided to a fractionation step, where it is fractionated into different ethyleneamine product fractions, and an ethyleneamine compound fraction is withdrawn from the elimination step in the first reaction sequence and provided to said fractionation step from the second reaction sequence and/or a product withdrawn from a separation step in the first reaction sequence is provided to the fractionation step in the second reaction sequence.

This combination of providing one or more fractions from the fractionation step in the second reaction sequence to the first reaction sequence and vice versa allows a particularly efficient use of equipment, and makes it possible to tailor the nature of the products produced to the market demand. It is possible to have either or both of streams as illustrated by 401 and 402 and either or both of streams as illustrated by 403 and 404.

FIG. 2B illustrates a further embodiment of the present disclosure. In addition to lines 401, 402, 403, and 404 from FIG. 2A, FIG. 2B also encompasses the following lines:

405 ethyleneamine compound from chain extension step to step to amination reaction step 406 ethyleneamine compound from chain extension step to step to separation step 407 ethyleneamine compound from elimination step to amination reaction step 408 ethyleneamine compound from separation step of first sequence to amination reaction step As will be evident to the skilled person, it is not necessary to have all these lines in combination. This is certainly possible, however. It is within the scope of the skilled person to select which streams best match the desired product profile, also taking the available starting materials into account.

FIG. 3 illustrates an embodiment of the present disclosure in which a step of the first reaction sequence and a step of the second reaction sequence are combined. More in particular, effluent from the elimination step 7 and effluent from the amination step 200 are both provided to a separation step 208. In separation step 208, a number of different streams are generated, examples of which are illustrated in FIG. 3. A first fraction comprising ammonia and optionally hydrogen is withdrawn through line 209. This fraction can, if so desired, be recycled in whole or in part to amination step 200. A further fraction comprising relatively light components such as monoethanolamine and diethanolamine is withdrawn through line 210. This fraction can be provided in its entirety or in part, to one or more of amination step 200, adduction step 2, or chain extension reaction step 5, depending on the composition of the fraction, the products aimed for, and the starting materials available. A product fraction comprising compounds aimed for, e.g., one or more of diethylenetriamine (DETA), triethylenetetramine (TETA), and tetraethylenepentamine (TEPA) can be withdrawn through line 211. A fraction containing higher boiling compounds, e.g., compounds still comprising a cyclic urea moiety can be withdrawn through line 212. As will be evident to the skilled person, it is possible to have more or fewer streams generated by separation step 208. The four streams discussed here are examples only.

The use of a combined separation section as is illustrated in this embodiment enables more efficient use of separation equipment, and efficient tailoring of product fractions depending on prevailing market conditions.

Figure 4:
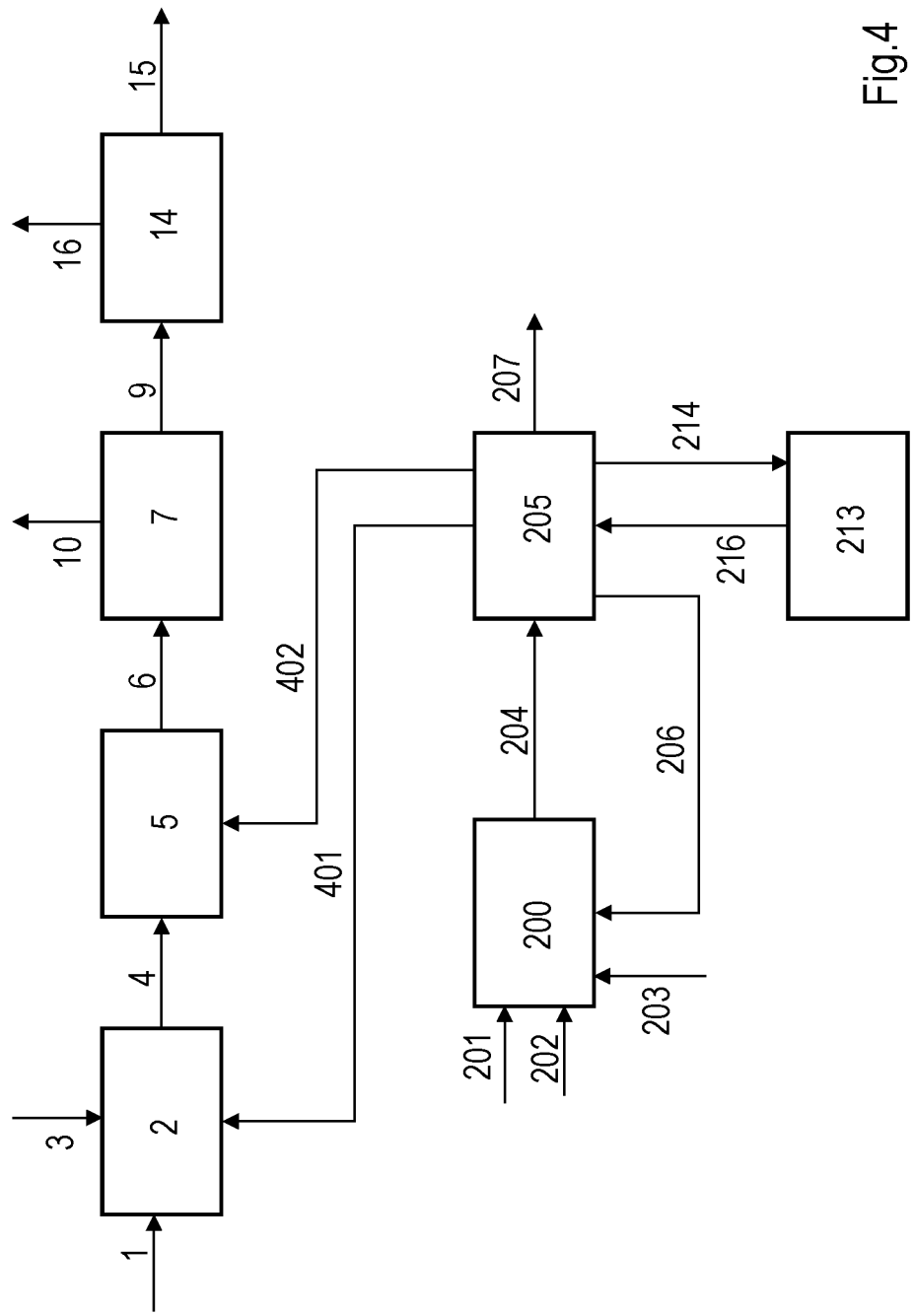
FIG. 4 illustrates a further embodiment of the process as contemplated herein.

FIG. 4 illustrates a variation on FIG. 1 wherein a transamination step 213 has been included. In this embodiment, an effluent stream comprising EDA is withdrawn from separation step 205 through line 214 and provided to transamination step 213, where it is reacted in the presence of a catalyst in contact with hydrogen provided through line 215. As will be evident to the skilled person, hydrogen does not have to be provided through a separate line. It can also be introduced in the step in combination with other streams. The same applies to the provision of hydrogen to amination step 200. Hydrogen streams in the process as contemplated herein can derive from the same or different sources. Hydrogen can be recycled as desired. Monoethanolamine may be provided through lines not shown. The reaction product comprising higher ethanolamines is provided to separation step 205 through line 216.

In the embodiment illustrated here, the effluent from amination step 200 and transamination step 213 are both coupled separately to separation step 205. As will be evident to the skilled person, it is also possible to carry out, sequentially, an amination step, a separation step, a transamination step, and a further separation step.

As will also be clear to the skilled person it is also possible to provide effluent streams comprising EDA which derive from other sources to the transamination step. Examples include streams comprising EDA derived from the chain extension reaction step, the elimination step, and the separation step.

Figure 5:
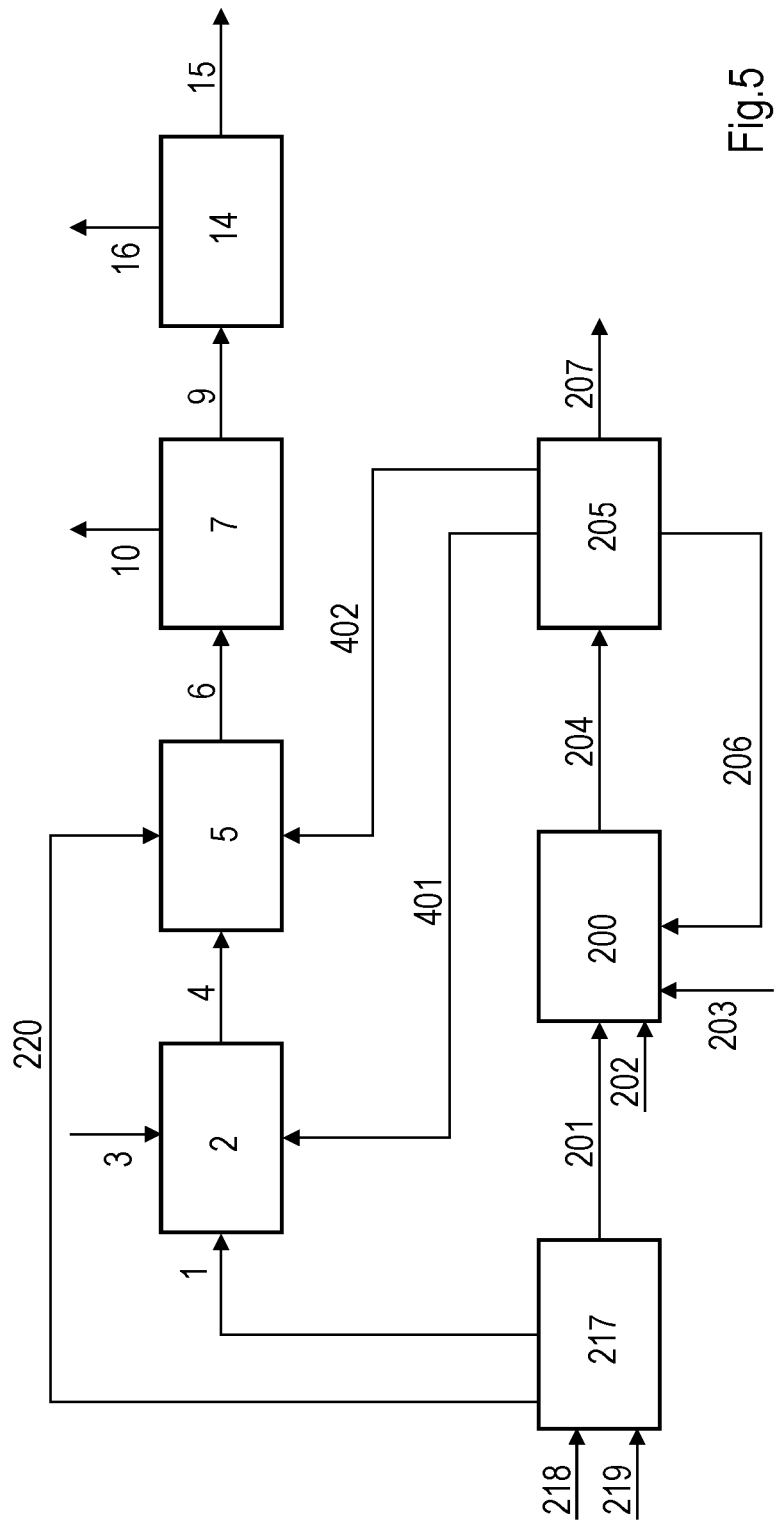
FIG. 5 illustrates a further embodiment of the process as contemplated herein.

The process of this embodiment containing two amination steps makes it possible to manufacture an increased amount of higher ethyleneamine compounds in a controlled and efficient manner Additionally, the presence of two amination steps in the second reaction sequence in combination with the first reaction sequence makes for increased process flexibility, by being able to increase the capacity for manufacturing higher ethyleneamines (which are mainly produced in the chain extension step in the first reaction sequence and in the second amination step in the second reaction sequence) on demand FIG. 5 shows a further embodiment of the present disclosure, which also comprises an ethyleneoxide conversion unit 217. In ethyleneoxide conversion unit 217 ethyleneoxide provided through line 218 is reacted with ammonia provided through line 219, to form monoethanolamine. The monoethanolamine can be provided as starting material to the amination step 200 through line 201. It can also be provided to the adduction step 2 through line 1, or to the chain extension reaction step 5 through line 220, whichever is desired. The ammonia from line 219 can be derived from the same source as the ammonia provided through line 202, or from a different source. It can also be derived from separation step 205 through a line not shown.

Streams 401 and 402 are not necessary in this embodiment, but their presence is advantageous for the reasons discussed for FIG. 1 above. The use of ammonia and ethyleneoxide as illustrated in this figure can advantageously be combined with the recycle of compounds through one or more of lines 401, 402 403, 404, 405, 406, 407, and 408 as illustrated in FIGS. 2A and 2B. As will be evident to the skilled person, it is not necessary to have all these lines in combination. This is certainly possible, however. It is within the scope of the skilled person to select which streams best match the desired product profile, also taking the available starting materials into account.

The embodiment of the disclosure of which FIG. 5 is an illustration makes it possible to use ammonia and ethyleneoxide as starting materials for a variety of high-value ethyleneamine products.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims

REFERENCE LIST 1 starting compound comprising a —NH—CH2-CH2-NH— moiety or a —NH—CH2-CH2-OH moiety, or HO—CH2-CH2-OH
2 adduction step
3 carbon oxide delivering agent, e.g., CO2
4 effluent from adduction step
5 chain extension reaction step
6 effluent from chain extension reaction step
7 elimination step
9 ethyleneamine compound
10 compound comprising carbonyl group
14 separation step
15 ethyleneamine compound product fraction
16 starting materials and/or intermediate products
200 amination reaction step
201 provision of monoethanolamine 202 ammonia
203 hydrogen
204 product mixture from amination reaction step
205 separation step
206 recycle stream of ammonia and optionally hydrogen
207 product stream
208 separation step
209 fraction comprising ammonia and optionally hydrogen
210 fraction comprising light components
211 product fraction
212 fraction containing higher-boiling components
213 transamination step
214 effluent stream comprising EDA
215 hydrogen
216 product of transamination step
217 ethyleneoxide conversion unit
218 ethyleneoxide
219 ammonia
220 MEA
401 ethyleneamine compound to adduction step
402 ethyleneamine compound to chain extension reaction step
403 ethyleneamine compound from elimination step to separation step
404 ethyleneamine compound from separation step of first sequence to separation step of second sequence
405 ethyleneamine compound from chain extension step to step to amination reaction step
406 ethyleneamine compound from chain extension step to step to separation step
407 ethyleneamine compound from elimination step to amination reaction step
408 ethyleneamine compound from separation step of first sequence to amination reaction step

What is claimed is:

1. Process for manufacturing ethyleneamine compounds selected from the group of ethyleneamines and hydroxyethylethyleneamines, wherein the process comprises two reaction sequences, the first reaction sequence comprising the steps of:
in an adduction step, providing a $CO_2$ adduct of a starting compound comprising a —NH—CH2-CH2-NH— moiety or a —NH—CH2-CH2-OH moiety, or HO—CH2-CH2-OH,
in a chain-extension step, reacting a hydroxy-functional compound selected from ethanolamines and dihydroxyethane with an ethyleneamine compound, wherein at least part of a total of hydroxy-functional compounds and the ethyleneamine compound is provided in the form of a $CO_2$ adduct, to form a $CO_2$ adduct of a chain-extended ethyleneamine compound,
in an elimination step, converting the $CO_2$ adduct of the chain-extended ethyleneamine compound to the corresponding product ethyleneamine compound by removal of the carbonyl group, and the second reaction sequence comprising the steps of:
in an amination step, reacting monoethanolamine with ammonia in the presence of hydrogen and an amination catalyst to form a reaction mixture comprising ethylenediamine,
in a separation step, separating the reaction mixture derived from the amination step into at least two fractions, wherein the first reaction sequence and the second reaction sequence are connected in that at least one of the following takes place:
an effluent from a step in the first reaction sequence is provided as a starting material to a step in the second reaction sequence,
an effluent from a step in the second reaction sequence is provided as a starting material to a step in the first reaction sequence,
a step of the first reaction sequence and a step of the second reaction sequence are combined, or
an effluent from a step in the first reaction sequence is combined with an effluent from a step in the second reaction sequence.

2. Process according to claim 1, wherein product from the amination step is provided to the adduction step or the chain-extension step in the first reaction sequence, directly, or with an intermediate separation step being carried out.

3. Process according to claim 1, wherein product from the amination step and product from the elimination step are combined and provided to the separation step.

4. Process according to claim 1, wherein the elimination step in the first reaction sequence comprises a distillation step, and a product from the amination step is provided to the distillation step.

5. Process according to claim 1, wherein the second reaction sequence comprises at least one further amination step wherein an ethyleneamine reactant is reacted with a compound selected from ammonia or a further ethyleneamine reactant in the presence of hydrogen and an amination catalyst.

6. Process according to claim 5, wherein the further amination step comprises a step selected from
an amination step wherein ethylene diamine is reacted to form higher ethyleneamines; and
an amination step wherein ethylene diamine is reacted with monoethanolamine to form higher ethyleneamines.

7. Process according to claim 4, wherein the second reaction sequence comprises at least two amination steps wherein in a first amination step monoethanolamine is reacted with ammonia to form ethylenediamine, and in a second amination step ethylenediamine is reacted in the presence of hydrogen and an amination catalyst to form higher ethyleneamines that include more ethylene moieties than ethylenediamine moieties.

8. Process according to claim 7, wherein ethylene diamine is produced in the first amination step and is provided as starting material to the second amination step, directly or from an intermediate separation step.

9. Process according to claim 5, wherein a product from the further amination step and product from the elimination step are combined and provided to a separation step.

10. Process according to claim 5, wherein the elimination step in the first reaction sequence comprises a distillation step, and a product from the further amination step is provided to the distillation step in the elimination step.

11. Process according to claim 1, wherein a product from the first reaction sequence and a product from the second reaction sequence are provided to a single purification step.

12. Process according to claim 1, further comprising an ethyleneoxide conversion step wherein ethyleneoxide and ammonia are reacted to produce monoethanolamine, and the monoethanolamine is provided to one or more of
the amination step,
the adduction step, and/or
the chain extension reaction step.

13. Process according to claim 1, wherein ethylenediamine or aminoethylethanolamine is produced in the amination step and is provided to the adduction step or the chain-extension step in the first reaction sequence, directly, or with an intermediate separation step being carried out.

14. Process according to claim 1, wherein a product from the chain elongation step of the first reaction sequence is provided to one or more of the amination reaction step and the separation step of the second reaction sequence.

15. Process according to claim 1, wherein a product from the elimination step or an optional separating step from the first reaction sequence is provided to the amination step.

16. Process according to claim 1, which comprises the step of reacting ethyleneoxide and ammonia to form monoethanolamine, wherein a first part of the monoethanolamine is provided to the amination step in the second reaction sequence and reacted with ammonia to form ethylene diamine, wherein the ethylene diamine is provided at least in part to the adduction step or the chain-extension step of the first reaction sequence, and wherein a second part of the monoethanolamine is provided to the adduction step or the chain-extension step of the first reaction sequence.

* * * * *